US012287335B2

(12) United States Patent
Molhoj et al.

(10) Patent No.: US 12,287,335 B2
(45) Date of Patent: *Apr. 29, 2025

(54) DIRECT AFFINITY MEASUREMENT OF HUMAN IgG1 BINDING MULTIMERIC ANTIGENS

(71) Applicant: Hoffmann-La Roche Inc., Little Falls, NJ (US)

(72) Inventors: Michael Molhoj, Munich (DE);
Christian Gassner, Penzberg (DE);
Joerg Moelleken, Munich (DE);
Manuel Endesfelder, Wessling (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 889 days.

This patent is subject to a terminal disclaimer.

(21) Appl. No.: 17/062,279

(22) Filed: Oct. 2, 2020

(65) Prior Publication Data

US 2021/0199653 A1 Jul. 1, 2021

Related U.S. Application Data

(63) Continuation of application No. 16/003,450, filed on Jun. 8, 2018, now abandoned, which is a continuation of application No. PCT/EP2016/079756, filed on Dec. 5, 2016.

(30) Foreign Application Priority Data

Dec. 9, 2015 (EP) ...................... 15198556

(51) Int. Cl.
| | | |
|---|---|---|
| *G01N 31/00* | (2006.01) | |
| *C07K 16/00* | (2006.01) | |
| *C07K 16/12* | (2006.01) | |
| *C07K 16/22* | (2006.01) | |
| *C12Q 1/37* | (2006.01) | |
| *G01N 21/552* | (2014.01) | |
| *G01N 33/53* | (2006.01) | |
| *G01N 33/537* | (2006.01) | |
| *G01N 33/557* | (2006.01) | |
| *G01N 33/566* | (2006.01) | |
| *G01N 33/569* | (2006.01) | |
| *G01N 33/68* | (2006.01) | |

(52) U.S. Cl.
CPC .......... *G01N 33/557* (2013.01); *C07K 16/00* (2013.01); *C07K 16/1203* (2013.01); *C07K 16/22* (2013.01); *C12Q 1/37* (2013.01); *G01N 21/553* (2013.01); *G01N 33/5375* (2013.01); *G01N 33/566* (2013.01); *G01N 33/56911* (2013.01); *G01N 33/56955* (2013.01); *G01N 33/6857* (2013.01); *C07K 2317/31* (2013.01); *C07K 2317/35* (2013.01); *C07K 2317/52* (2013.01); *C07K 2317/55* (2013.01); *C07K 2317/92* (2013.01); *G01N 2333/96466* (2013.01)

(58) Field of Classification Search
None
See application file for complete search history.

(56) References Cited

U.S. PATENT DOCUMENTS 11,958,912 B2 * 4/2024 Moelleken ......... G01N 33/6857
2014/0288007 A1 9/2014 Dashper et al.

FOREIGN PATENT DOCUMENTS

| JP | 2007-016002 | | 1/2007 | |
|---|---|---|---|---|
| WO | 95/11298 A1 | | 4/1995 | |
| WO | 2004/106541 | | 12/2004 | |
| WO | WO-2012130831 A1 * | 10/2012 | ........... A61K 39/395 |
| WO | 2013/063656 A1 | | 5/2013 | |
| WO | 2015/040125 A1 | | 3/2015 | |

OTHER PUBLICATIONS

Moelleken et al. (MABS, 2017, vol. 9, No. 7, pp. 1076-1087) (Year: 2017).*
Guentsch et al., "Cleavage of IgG1 in gingival crevicular fluid is associated with the presence of Porphyromonas gingivalis" Journal of Periodontal Research 48:458-465. 2013. (Year: 2013) (Year: 2013).*
pp. 1 (Genovis—GingisKHAN instructions 2015).
pp. 1-4 (Genovis_Applications—IgG Protease Digestion Chart 2015).
pp. 1-6 (Genovis Applications 2015).
pp. 1-7 (Genovis—GingisKHAN KGP protease 2015).
Arai et al., "BIACORE™, a System for Biomolecular Interaction Analysis Using Surface Plasmon Resonance:" Japanese J Thrombosis, 8(5):397-405 ( 1997).
De Diego, I., et al., "Structure and Mechanism of Cysteine Peptidase Gingipain K (Kgp), a Major Virulence Factor of Porphyromonas gingivalis in Periodontitis" J Biol Chem 289(46):32291-32302 (Sep. 29, 2014).
Dillon, T., et al., "Development of an analytical reversed-phase high-performance liquid chromatography-electrospray ionization mass spectrometry method for characterization of recombinant antibodies" J Chromatog A 1053(1-2):299-305 (Oct. 22, 2004).

(Continued)

Primary Examiner — Lisa V Cook
(74) Attorney, Agent, or Firm — GENENTECH, INC.

(57) ABSTRACT

Herein is reported a method for determining the binding affinity of the binding sites of a bivalent full length antibody of the human IgG1 subclass to a homo-multimeric antigen comprising the steps of i) incubating a mixture comprising the antibody and a polypeptide that is derived from lysine-gingipain of *Porphyromonas gingivalis* at a pH of from pH 7.5 to pH 8.5, in the presence of a reducing agent, at a temperature of from 30° C. to 42° C., for time of from 10 min. to 240 min. to cleave the antibody into Fabs and Fc-region, and ii) determining the binding affinity of the Fabs of the antibody for its antigen using a surface plasmon resonance method by directly applying the incubated reaction mixture obtained in the previous step in the surface plasmon resonance method and therewith determining the binding affinity of the binding sites of the bivalent full length antibody of the human IgG1 subclass.

22 Claims, 7 Drawing Sheets
Specification includes a Sequence Listing.

(56) References Cited

OTHER PUBLICATIONS

Guentsch et al., "Cleavage of IgG1 in gingival crevicular fluid is associated with the presence of Porphyromonas gingivalis" Journal of Periodontal Research 48:458-465.

Inagaki, S., et al., "Antibody Responses of Periodontitis Patients to Gingipains of Porphyromonas gingivalis" J Periodontol 74(10):1432-1439 (Oct. 1, 2003).

ISR and Written Opinion of PCT/EP2016/079756 (Date of mailing Jan. 16, 2017).

Kadowaki, T., et al., "Purification and Characterization of a Novel Arginine-specific" J Biol Chem 269(33):21371-21378 (Aug. 19, 1994).

Kikuchi, Y. et al., "Determination of concentration and binding affinity of antibody fragments by use of surface plasmon resonance" J Biosci Bioeng 100(3):311-317 (Sep. 1, 2005).

Lottspeich and Engels BIOANALYTIK (Spektrum Akademischer Verlag), 2nd edition, Munich::201-214 (2006).

Moelleken, J., et al., "GingisKHAN protease cleavage allows a high-throughput antibody to Fab conversion enabling direct functional assessment during lead identification of human monoclonal and bispecific igGI antibodies" MABS 9(7):1076-1087 (Aug. 14, 2017).

Nguyen, H., et al., "Surface Plasmon Resonance: A Versatile Technique for Biosensor Applications" Sensors—BASEL 15(5):10481-10510 (May 5, 2015).

Schomburg Handbook of Enzymes—Class 3 Hydrolases "Gingipain K" Springer Verlag, vol. Supplemental S6:1-10 ( 2009).

Simpson, W., et al., "Lysine-specific gingipain K and heme/hemoglobin receptor HmuR are involved in heme utilization in Porphyromonas gingivalis" Acta Biochim Pol 51(1):253-262 (2004).

Sztukowska, M., et al., "The C-terminal domains of the gingipain K polyprotein are necessary for assembly of the active enzyme and expression of associated activities" Mol Microbiol 54(5):1393-1408 (Dec. 1, 2004).

Vincents, B., et al., "Cleavage of IgG1 and IgG3 by gingipain K from Porphyromonas gingivalis may compromise host defense in progressive periodontitis" FASEB J 25(10):3741-3750 (Oct. 1, 2011).

Vincents, B., et al., "Enzymatic characterization of the streptococcal endopeptidase, IdeS, reveals that it is a cysteine protease with strict specificity for IgG cleavage due to exosite binding" Biochemistry 43(49):15540-15549 (Dec. 14, 2004).

Von Pawel-Rammingen, U., et al., "IdeS, a novel streptococcal cysteine proteinase with unique specificity for immunoglobulin G" EMBO J 21(7):1607-1615 (Apr. 2, 2002).

\* cited by examiner

SEQUENCE LISTING

<160> NUMBER OF SEQ ID NOS: 7

<210> SEQ ID NO 1
<211> LENGTH: 1733
<212> TYPE: PRT
<213> ORGANISM: Porphyromonas gingivalis

<400> SEQUENCE: 1

Met Arg Lys Leu Leu Leu Leu Ile Ala Ala Ser Leu Leu Gly Val Gly
1               5                   10                  15

Leu Tyr Ala Gln Ser Ala Lys Ile Lys Leu Asp Ala Pro Thr Thr Arg
            20                  25                  30

Thr Thr Cys Thr Asn Asn Ser Phe Lys Gln Phe Asp Ala Ser Phe Ser
        35                  40                  45

Phe Asn Glu Val Glu Leu Thr Lys Val Glu Thr Lys Gly Gly Thr Phe
    50                  55                  60

Ala Ser Val Ser Ile Pro Gly Ala Phe Pro Thr Gly Glu Val Gly Ser
65                  70                  75                  80

Pro Glu Val Pro Ala Val Arg Lys Leu Ile Ala Val Pro Val Gly Ala
                85                  90                  95

Thr Pro Val Val Arg Val Lys Ser Phe Thr Gln Val Tyr Ser Leu
            100                 105                 110

Asn Gln Tyr Gly Ser Glu Lys Leu Met Pro His Gln Pro Ser Met Ser
            115                 120                 125

Lys Ser Asp Asp Pro Glu Lys Val Pro Phe Val Tyr Asn Ala Ala Ala
    130                 135                 140

Tyr Ala Arg Lys Gly Phe Val Gly Gln Glu Leu Thr Gln Val Glu Met
145                 150                 155                 160

Leu Gly Thr Met Arg Gly Val Arg Ile Ala Ala Leu Thr Ile Asn Pro
                165                 170                 175

Val Gln Tyr Asp Val Val Ala Asn Gln Leu Lys Val Arg Asn Asn Ile
            180                 185                 190

Glu Ile Glu Val Ser Phe Gln Gly Ala Asp Glu Val Ala Thr Gln Arg
            195                 200                 205

Leu Tyr Asp Ala Ser Phe Ser Pro Tyr Phe Glu Thr Ala Tyr Lys Gln
    210                 215                 220

Leu Phe Asn Arg Asp Thr Val Tyr Thr Asp His Gly Asp Leu Tyr Asn

```
              225                 230                 235                 240
Thr Pro Val Arg Met Leu Val Ala Gly Ala Lys Phe Lys Glu Ala
                    245                 250                 255
Leu Lys Pro Trp Leu Thr Trp Lys Ala Gln Lys Gly Phe Tyr Leu Asp
                    260                 265                 270
Val His Tyr Thr Asp Glu Ala Glu Val Gly Thr Thr Asn Ala Ser Ile
                275                 280                 285
Lys Ala Phe Ile His Lys Lys Tyr Asn Asp Gly Leu Ala Ala Ser Ala
            290                 295                 300
Ala Pro Val Phe Leu Ala Leu Val Gly Asp Thr Asp Val Ile Ser Gly
305                 310                 315                 320
Glu Lys Gly Lys Lys Thr Lys Lys Val Thr Asp Leu Tyr Tyr Ser Ala
                    325                 330                 335
Val Asp Gly Asp Tyr Phe Pro Glu Met Tyr Thr Phe Arg Met Ser Ala
                340                 345                 350
Ser Ser Pro Glu Glu Leu Thr Asn Ile Ile Asp Lys Val Leu Met Tyr
            355                 360                 365
Glu Lys Ala Thr Met Pro Asp Lys Ser Tyr Leu Glu Lys Val Leu Leu
        370                 375                 380
Ile Ala Gly Ala Asp Tyr Ser Trp Asn Ser Gln Val Gly Gln Pro Thr
385                 390                 395                 400
Ile Lys Tyr Gly Met Gln Tyr Tyr Asn Gln Glu His Gly Tyr Thr
                    405                 410                 415
Asp Val Tyr Asn Tyr Leu Lys Ala Pro Tyr Thr Gly Cys Tyr Ser His
                420                 425                 430
Leu Asn Thr Gly Val Ser Phe Ala Asn Tyr Thr Ala His Gly Ser Glu
            435                 440                 445
Thr Ala Trp Ala Asp Pro Leu Leu Thr Thr Ser Gln Leu Lys Ala Leu
        450                 455                 460
Thr Asn Lys Asp Lys Tyr Phe Leu Ala Ile Gly Asn Cys Cys Ile Thr
465                 470                 475                 480
Ala Gln Phe Asp Tyr Val Gln Pro Cys Phe Gly Glu Val Ile Thr Arg
                    485                 490                 495
Val Lys Glu Lys Gly Ala Tyr Ala Tyr Ile Gly Ser Ser Pro Asn Ser
                500                 505                 510
Tyr Trp Gly Glu Asp Tyr Tyr Trp Ser Val Gly Ala Asn Ala Val Phe
            515                 520                 525
Gly Val Gln Pro Thr Phe Glu Gly Thr Ser Met Gly Ser Tyr Asp Ala
        530                 535                 540
Thr Phe Leu Glu Asp Ser Tyr Asn Thr Val Asn Ser Ile Met Trp Ala
545                 550                 555                 560
Gly Asn Leu Ala Ala Thr His Ala Gly Asn Ile Gly Asn Ile Thr His
                    565                 570                 575
Ile Gly Ala His Tyr Tyr Trp Glu Ala Tyr His Val Leu Gly Asp Gly
                580                 585                 590
Ser Val Met Pro Tyr Arg Ala Met Pro Lys Thr Asn Thr Tyr Thr Leu
            595                 600                 605
Pro Ala Ser Leu Pro Gln Asn Gln Ala Ser Tyr Ser Ile Gln Ala Ser
        610                 615                 620
Ala Gly Ser Tyr Val Ala Ile Ser Lys Asp Gly Val Leu Tyr Gly Thr
625                 630                 635                 640
Gly Val Ala Asn Ala Ser Gly Val Ala Thr Val Ser Met Thr Lys Gln
                    645                 650                 655
```

```
Ile Thr Glu Asn Gly Asn Tyr Asp Val Val Ile Thr Arg Ser Asn Tyr
            660                 665                 670

Leu Pro Val Ile Lys Gln Ile Val Gly Glu Pro Ser Pro Tyr Gln
        675                 680                 685

Pro Val Ser Asn Leu Thr Ala Thr Thr Gln Gly Gln Lys Val Thr Leu
    690                 695                 700

Lys Trp Glu Ala Pro Ser Ala Lys Lys Ala Glu Gly Ser Arg Glu Val
705                 710                 715                 720

Lys Arg Ile Gly Asp Gly Leu Phe Val Thr Ile Glu Pro Ala Asn Asp
                725                 730                 735

Val Arg Ala Asn Glu Ala Lys Val Val Leu Ala Ala Asp Asn Val Trp
            740                 745                 750

Gly Asp Asn Thr Gly Tyr Gln Phe Leu Leu Asp Ala Asp His Asn Thr
        755                 760                 765

Phe Gly Ser Val Ile Pro Ala Thr Gly Pro Leu Phe Thr Gly Thr Ala
    770                 775                 780

Ser Ser Asn Leu Tyr Ser Ala Asn Phe Glu Tyr Leu Ile Pro Ala Asn
785                 790                 795                 800

Ala Asp Pro Val Val Thr Thr Gln Asn Ile Ile Val Thr Gly Gln Gly
                805                 810                 815

Glu Val Val Ile Pro Gly Gly Val Tyr Asp Tyr Cys Ile Thr Asn Pro
            820                 825                 830

Glu Pro Ala Ser Gly Lys Met Trp Ile Ala Gly Asp Gly Asn Gln
        835                 840                 845

Pro Ala Arg Tyr Asp Asp Phe Thr Phe Glu Ala Gly Lys Lys Tyr Thr
    850                 855                 860

Phe Thr Met Arg Arg Ala Gly Met Gly Asp Gly Thr Asp Met Glu Val
865                 870                 875                 880

Glu Asp Asp Ser Pro Ala Ser Tyr Thr Tyr Thr Val Tyr Arg Asp Gly
                885                 890                 895

Thr Lys Ile Lys Glu Gly Leu Thr Ala Thr Thr Phe Glu Glu Asp Gly
            900                 905                 910

Val Ala Ala Gly Asn His Glu Tyr Cys Val Glu Val Lys Tyr Thr Ala
        915                 920                 925

Gly Val Ser Pro Lys Val Cys Lys Asp Val Thr Val Glu Gly Ser Asn
    930                 935                 940

Glu Phe Ala Pro Val Gln Asn Leu Thr Gly Ser Ser Val Gly Gln Lys
945                 950                 955                 960

Val Thr Leu Lys Trp Asp Ala Pro Asn Gly Thr Asn Pro Asn Pro
                965                 970                 975

Asn Pro Asn Pro Asn Pro Gly Thr Thr Leu Ser Glu Ser Phe Glu Asn
            980                 985                 990

Gly Ile Pro Ala Ser Trp Lys Thr Ile Asp Ala Asp Gly Asp Gly His
        995                 1000                1005

Gly Trp Lys Pro Gly Asn Ala Pro Gly Ile Ala Gly Tyr Asn Ser
    1010                1015                1020

Asn Gly Cys Val Tyr Ser Glu Ser Phe Gly Leu Gly Gly Ile Gly
    1025                1030                1035

Val Leu Thr Pro Asp Asn Tyr Leu Ile Thr Pro Ala Leu Asp Leu
    1040                1045                1050

Pro Asn Gly Gly Lys Leu Thr Phe Trp Val Cys Ala Gln Asp Ala
    1055                1060                1065
```

-continued

Asn Tyr Ala Ser Glu His Tyr Ala Val Tyr Ala Ser Ser Thr Gly
1070             1075                 1080

Asn Asp Ala Ser Asn Phe Thr Asn Ala Leu Leu Glu Glu Thr Ile
1085             1090                 1095

Thr Ala Lys Gly Val Arg Ser Pro Lys Ala Ile Arg Gly Arg Ile
1100             1105                 1110

Gln Gly Thr Trp Arg Gln Lys Thr Val Asp Leu Pro Ala Gly Thr
1115             1120                 1125

Lys Tyr Val Ala Phe Arg His Phe Gln Ser Thr Asp Met Phe Tyr
1130             1135                 1140

Ile Asp Leu Asp Glu Val Glu Ile Lys Ala Asn Gly Lys Arg Ala
1145             1150                 1155

Asp Phe Thr Glu Thr Phe Glu Ser Ser Thr His Gly Glu Ala Pro
1160             1165                 1170

Ala Glu Trp Thr Thr Ile Asp Ala Asp Gly Asp Gly Gln Gly Trp
1175             1180                 1185

Leu Cys Leu Ser Ser Gly Gln Leu Asp Trp Leu Thr Ala His Gly
1190             1195                 1200

Gly Ser Asn Val Val Ser Ser Phe Ser Trp Asn Gly Met Ala Leu
1205             1210                 1215

Asn Pro Asp Asn Tyr Leu Ile Ser Lys Asp Val Thr Gly Ala Thr
1220             1225                 1230

Lys Val Lys Tyr Tyr Tyr Ala Val Asn Asp Gly Phe Pro Gly Asp
1235             1240                 1245

His Tyr Ala Val Met Ile Ser Lys Thr Gly Thr Asn Ala Gly Asp
1250             1255                 1260

Phe Thr Val Val Phe Glu Glu Thr Pro Asn Gly Ile Asn Lys Gly
1265             1270                 1275

Gly Ala Arg Phe Gly Leu Ser Thr Glu Ala Asn Gly Ala Lys Pro
1280             1285                 1290

Gln Ser Val Trp Ile Glu Arg Thr Val Asp Leu Pro Ala Gly Thr
1295             1300                 1305

Lys Tyr Val Ala Phe Arg His Tyr Asn Cys Ser Asp Leu Asn Tyr
1310             1315                 1320

Ile Leu Leu Asp Asp Ile Gln Phe Thr Met Gly Gly Ser Pro Thr
1325             1330                 1335

Pro Thr Asp Tyr Thr Tyr Thr Val Tyr Arg Asp Gly Thr Lys Ile
1340             1345                 1350

Lys Glu Gly Leu Thr Glu Thr Phe Glu Glu Asp Gly Val Ala
1355             1360                 1365

Thr Gly Asn His Glu Tyr Cys Val Glu Val Lys Tyr Thr Ala Gly
1370             1375                 1380

Val Ser Pro Lys Lys Cys Val Asn Val Thr Val Asn Ser Thr Gln
1385             1390                 1395

Phe Asn Pro Val Gln Asn Leu Thr Ala Glu Gln Ala Pro Asn Ser
1400             1405                 1410

Met Asp Ala Ile Leu Lys Trp Asn Ala Pro Ala Ser Lys Arg Ala
1415             1420                 1425

Glu Val Leu Asn Glu Asp Phe Glu Asn Gly Ile Pro Ala Ser Trp
1430             1435                 1440

Lys Thr Ile Asp Ala Asp Gly Asp Gly Asn Asn Trp Thr Thr Thr
1445             1450                 1455

Pro Pro Pro Gly Gly Ser Ser Phe Ala Gly His Asn Ser Ala Ile

```
            1460                1465                1470
Cys Val Ser Ser Ala Ser Tyr Ile Asn Phe Glu Gly Pro Gln Asn
        1475                1480                1485

Pro Asp Asn Tyr Leu Val Thr Pro Glu Leu Ser Leu Pro Gly Gly
    1490                1495                1500

Gly Thr Leu Thr Phe Trp Val Cys Ala Gln Asp Ala Asn Tyr Ala
    1505                1510                1515

Ser Glu His Tyr Ala Val Tyr Ala Ser Ser Thr Gly Asn Asp Ala
    1520                1525                1530

Ser Asn Phe Ala Asn Ala Leu Leu Glu Glu Val Leu Thr Ala Lys
    1535                1540                1545

Thr Val Val Thr Ala Pro Glu Ala Ile Arg Gly Thr Arg Ala Gln
    1550                1555                1560

Gly Thr Trp Tyr Gln Lys Thr Val Gln Leu Pro Ala Gly Thr Lys
    1565                1570                1575

Tyr Val Ala Phe Arg His Phe Gly Cys Thr Asp Phe Phe Trp Ile
    1580                1585                1590

Asn Leu Asp Asp Val Val Ile Thr Ser Gly Asn Ala Pro Ser Tyr
    1595                1600                1605

Thr Tyr Thr Ile Tyr Arg Asn Asn Thr Gln Ile Ala Ser Gly Val
    1610                1615                1620

Thr Glu Thr Thr Tyr Arg Asp Pro Asp Leu Ala Thr Gly Phe Tyr
    1625                1630                1635

Thr Tyr Gly Val Lys Val Tyr Pro Asn Gly Glu Ser Ala Ile
    1640                1645                1650

Glu Thr Ala Thr Leu Asn Ile Thr Ser Leu Ala Asp Val Thr Ala
    1655                1660                1665

Gln Lys Pro Tyr Thr Leu Thr Val Val Gly Lys Thr Ile Thr Val
    1670                1675                1680

Thr Cys Gln Gly Glu Ala Met Ile Tyr Asp Met Asn Gly Arg Arg
    1685                1690                1695

Leu Ala Ala Gly Arg Asn Thr Val Val Tyr Thr Ala Gln Gly Gly
    1700                1705                1710

His Tyr Ala Val Met Val Val Val Asp Gly Lys Ser Tyr Val Glu
    1715                1720                1725

Lys Leu Ala Val Lys
    1730

<210> SEQ ID NO 2
<211> LENGTH: 509
<212> TYPE: PRT
<213> ORGANISM: Porphyromonas gingivalis

<400> SEQUENCE: 2

Asp Val Tyr Thr Asp His Gly Asp Leu Tyr Asn Thr Pro Val Arg Met
1               5                   10                  15

Leu Val Val Ala Gly Ala Lys Phe Lys Glu Ala Leu Lys Pro Trp Leu
                20                  25                  30

Thr Trp Lys Ala Gln Lys Gly Phe Tyr Leu Asp Val His Tyr Thr Asp
            35                  40                  45

Glu Ala Glu Val Gly Thr Thr Asn Ala Ser Ile Lys Ala Phe Ile His
        50                  55                  60

Lys Lys Tyr Asn Asp Gly Leu Ala Ala Ser Ala Ala Pro Val Phe Leu
65                  70                  75                  80
```

```
Ala Leu Val Gly Asp Thr Asp Val Ile Ser Gly Glu Lys Gly Lys Lys
                85                  90                  95

Thr Lys Lys Val Thr Asp Leu Tyr Tyr Ser Ala Val Asp Gly Asp Tyr
            100                 105                 110

Phe Pro Glu Met Tyr Thr Phe Arg Met Ser Ala Ser Ser Pro Glu Glu
            115                 120                 125

Leu Thr Asn Ile Ile Asp Lys Val Leu Met Tyr Glu Lys Ala Thr Met
            130                 135                 140

Pro Asp Lys Ser Tyr Leu Glu Lys Val Leu Leu Ile Ala Gly Ala Asp
145                 150                 155                 160

Tyr Ser Trp Asn Ser Gln Val Gly Gln Pro Thr Ile Lys Tyr Gly Met
                165                 170                 175

Gln Tyr Tyr Tyr Asn Gln Glu His Gly Tyr Thr Asp Val Tyr Asn Tyr
                180                 185                 190

Leu Lys Ala Pro Tyr Thr Gly Cys Tyr Ser His Leu Asn Thr Gly Val
                195                 200                 205

Ser Phe Ala Asn Tyr Thr Ala His Gly Ser Glu Thr Ala Trp Ala Asp
            210                 215                 220

Pro Leu Leu Thr Thr Ser Gln Leu Lys Ala Leu Thr Asn Lys Asp Lys
225                 230                 235                 240

Tyr Phe Leu Ala Ile Gly Asn Cys Cys Ile Thr Ala Gln Phe Asp Tyr
                245                 250                 255

Val Gln Pro Cys Phe Gly Glu Val Ile Thr Arg Val Lys Glu Lys Gly
                260                 265                 270

Ala Tyr Ala Tyr Ile Gly Ser Ser Pro Asn Ser Tyr Trp Gly Glu Asp
            275                 280                 285

Tyr Tyr Trp Ser Val Gly Ala Asn Ala Val Phe Gly Val Gln Pro Thr
            290                 295                 300

Phe Glu Gly Thr Ser Met Gly Ser Tyr Asp Ala Thr Phe Leu Glu Asp
305                 310                 315                 320

Ser Tyr Asn Thr Val Asn Ser Ile Met Trp Ala Gly Asn Leu Ala Ala
                325                 330                 335

Thr His Ala Gly Asn Ile Gly Asn Ile Thr His Ile Gly Ala His Tyr
                340                 345                 350

Tyr Trp Glu Ala Tyr His Val Leu Gly Asp Gly Ser Val Met Pro Tyr
            355                 360                 365

Arg Ala Met Pro Lys Thr Asn Thr Tyr Thr Leu Pro Ala Ser Leu Pro
370                 375                 380

Gln Asn Gln Ala Ser Tyr Ser Ile Gln Ala Ser Ala Gly Ser Tyr Val
385                 390                 395                 400

Ala Ile Ser Lys Asp Gly Val Leu Tyr Gly Thr Gly Val Ala Asn Ala
                405                 410                 415

Ser Gly Val Ala Thr Val Ser Met Thr Lys Gln Ile Thr Glu Asn Gly
            420                 425                 430

Asn Tyr Asp Val Val Ile Thr Arg Ser Asn Tyr Leu Pro Val Ile Lys
            435                 440                 445

Gln Ile Gln Val Gly Glu Pro Ser Pro Tyr Gln Pro Val Ser Asn Leu
450                 455                 460

Thr Ala Thr Thr Gln Gly Gln Lys Val Thr Leu Lys Trp Glu Ala Pro
465                 470                 475                 480

Ser Ala Lys Lys Ala Glu Gly Ser Arg Glu Val Lys Arg Ile Gly Asp
                485                 490                 495

Gly Leu Phe Val Thr Ile Glu Pro Ala Asn Asp Val Arg
```

```
              500                 505

<210> SEQ ID NO 3
<211> LENGTH: 489
<212> TYPE: PRT
<213> ORGANISM: Porphyromonas gingivalis

<400> SEQUENCE: 3

Asp Val Tyr Thr Asp His Gly Asp Leu Tyr Asn Thr Pro Val Arg Met
1               5                   10                  15

Leu Val Val Ala Gly Ala Lys Phe Lys Glu Ala Leu Lys Pro Trp Leu
            20                  25                  30

Thr Trp Lys Ala Gln Lys Gly Phe Tyr Leu Asp Val His Tyr Thr Asp
        35                  40                  45

Glu Ala Glu Val Gly Thr Thr Asn Ala Ser Ile Lys Ala Phe Ile His
    50                  55                  60

Lys Lys Tyr Asn Asp Gly Leu Ala Ala Ser Ala Ala Pro Val Phe Leu
65                  70                  75                  80

Ala Leu Val Gly Asp Thr Asp Val Ile Ser Gly Glu Lys Gly Lys Lys
                85                  90                  95

Thr Lys Lys Val Thr Asp Leu Tyr Tyr Ser Ala Val Asp Gly Asp Tyr
            100                 105                 110

Phe Pro Glu Met Tyr Thr Phe Arg Met Ser Ala Ser Ser Pro Glu Glu
        115                 120                 125

Leu Thr Asn Ile Ile Asp Lys Val Leu Met Tyr Glu Lys Ala Thr Met
    130                 135                 140

Pro Asp Lys Ser Tyr Leu Glu Lys Val Leu Leu Ile Ala Gly Ala Asp
145                 150                 155                 160

Tyr Ser Trp Asn Ser Gln Val Gly Gln Pro Thr Ile Lys Tyr Gly Met
                165                 170                 175

Gln Tyr Tyr Tyr Asn Gln Glu His Gly Tyr Thr Asp Val Tyr Asn Tyr
            180                 185                 190

Leu Lys Ala Pro Tyr Thr Gly Cys Tyr Ser His Leu Asn Thr Gly Val
        195                 200                 205

Ser Phe Ala Asn Tyr Thr Ala His Gly Ser Glu Thr Ala Trp Ala Asp
    210                 215                 220

Pro Leu Leu Thr Thr Ser Gln Leu Lys Ala Leu Thr Asn Lys Asp Lys
225                 230                 235                 240

Tyr Phe Leu Ala Ile Gly Asn Cys Cys Ile Thr Ala Gln Phe Asp Tyr
                245                 250                 255

Val Gln Pro Cys Phe Gly Glu Val Ile Thr Arg Val Lys Glu Lys Gly
            260                 265                 270

Ala Tyr Ala Tyr Ile Gly Ser Ser Pro Asn Ser Tyr Trp Gly Glu Asp
        275                 280                 285

Tyr Tyr Trp Ser Val Gly Ala Asn Ala Val Phe Gly Val Gln Pro Thr
    290                 295                 300

Phe Glu Gly Thr Ser Met Gly Ser Tyr Asp Ala Thr Phe Leu Glu Asp
305                 310                 315                 320

Ser Tyr Asn Thr Val Asn Ser Ile Met Trp Ala Gly Asn Leu Ala Ala
                325                 330                 335

Thr His Ala Gly Asn Ile Gly Asn Ile Thr His Ile Gly Ala His Tyr
            340                 345                 350

Tyr Trp Glu Ala Tyr His Val Leu Gly Asp Gly Ser Val Met Pro Tyr
        355                 360                 365
```

-continued

```
Arg Ala Met Pro Lys Thr Asn Thr Tyr Thr Leu Pro Ala Ser Leu Pro
    370                 375                 380

Gln Asn Gln Ala Ser Tyr Ser Ile Gln Ala Ser Ala Gly Ser Tyr Val
385                 390                 395                 400

Ala Ile Ser Lys Asp Gly Val Leu Tyr Gly Thr Gly Val Ala Asn Ala
                405                 410                 415

Ser Gly Val Ala Thr Val Ser Met Thr Lys Gln Ile Thr Glu Asn Gly
                420                 425                 430

Asn Tyr Asp Val Val Ile Thr Arg Ser Asn Tyr Leu Pro Val Ile Lys
            435                 440                 445

Gln Ile Gln Val Gly Glu Pro Ser Pro Tyr Gln Pro Val Ser Asn Leu
    450                 455                 460

Thr Ala Thr Thr Gln Gly Gln Lys Val Thr Leu Lys Trp Glu Ala Pro
465                 470                 475                 480

Ser Ala Lys Lys Ala Glu Gly Ser Arg
                485

<210> SEQ ID NO 4
<211> LENGTH: 372
<212> TYPE: PRT
<213> ORGANISM: Porphyromonas gingivalis

<400> SEQUENCE: 4

Asp Val Tyr Thr Asp His Gly Asp Leu Tyr Asn Thr Pro Val Arg Met
1               5                   10                  15

Leu Val Val Ala Gly Ala Lys Phe Lys Glu Ala Leu Lys Pro Trp Leu
                20                  25                  30

Thr Trp Lys Ala Gln Lys Gly Phe Tyr Leu Asp Val His Tyr Thr Asp
            35                  40                  45

Glu Ala Glu Val Gly Thr Thr Asn Ala Ser Ile Lys Ala Phe Ile His
50                  55                  60

Lys Lys Tyr Asn Asp Gly Leu Ala Ala Ser Ala Ala Pro Val Phe Leu
65                  70                  75                  80

Ala Leu Val Gly Asp Thr Asp Val Ile Ser Gly Glu Lys Gly Lys Lys
                85                  90                  95

Thr Lys Lys Val Thr Asp Leu Tyr Tyr Ser Ala Val Asp Gly Asp Tyr
                100                 105                 110

Phe Pro Glu Met Tyr Thr Phe Arg Met Ser Ala Ser Pro Glu Glu
            115                 120                 125

Leu Thr Asn Ile Ile Asp Lys Val Leu Met Tyr Glu Lys Ala Thr Met
130                 135                 140

Pro Asp Lys Ser Tyr Leu Glu Lys Val Leu Leu Ile Ala Gly Ala Asp
145                 150                 155                 160

Tyr Ser Trp Asn Ser Gln Val Gly Gln Pro Thr Ile Lys Tyr Gly Met
                165                 170                 175

Gln Tyr Tyr Tyr Asn Gln Glu His Gly Tyr Thr Asp Val Tyr Asn Tyr
                180                 185                 190

Leu Lys Ala Pro Tyr Thr Gly Cys Tyr Ser His Leu Asn Thr Gly Val
    195                 200                 205

Ser Phe Ala Asn Tyr Thr Ala His Gly Ser Glu Thr Ala Trp Ala Asp
    210                 215                 220

Pro Leu Leu Thr Thr Ser Gln Leu Lys Ala Leu Thr Asn Lys Asp Lys
225                 230                 235                 240

Tyr Phe Leu Ala Ile Gly Asn Cys Cys Ile Thr Ala Gln Phe Asp Tyr
                245                 250                 255
```

```
Val Gln Pro Cys Phe Gly Glu Val Ile Thr Arg Val Lys Glu Lys Gly
            260                 265                 270

Ala Tyr Ala Tyr Ile Gly Ser Ser Pro Asn Ser Tyr Trp Gly Glu Asp
        275                 280                 285

Tyr Tyr Trp Ser Val Gly Ala Asn Ala Val Phe Gly Val Gln Pro Thr
    290                 295                 300

Phe Glu Gly Thr Ser Met Gly Ser Tyr Asp Ala Thr Phe Leu Glu Asp
305                 310                 315                 320

Ser Tyr Asn Thr Val Asn Ser Ile Met Trp Ala Gly Asn Leu Ala Ala
                325                 330                 335

Thr His Ala Gly Asn Ile Gly Asn Ile Thr His Ile Gly Ala His Tyr
            340                 345                 350

Tyr Trp Glu Ala Tyr His Val Leu Gly Asp Gly Ser Val Met Pro Tyr
        355                 360                 365

Arg Ala Met Pro
    370

<210> SEQ ID NO 5
<211> LENGTH: 21
<212> TYPE: PRT
<213> ORGANISM: Homo sapiens

<400> SEQUENCE: 5

Asp Lys Thr His Thr Cys Pro Pro Cys Pro Ala Pro Glu Leu Leu Gly
1               5                   10                  15

Gly Pro Ser Val Phe
            20

<210> SEQ ID NO 6
<211> LENGTH: 2
<212> TYPE: PRT
<213> ORGANISM: Artificial Sequence
<220> FEATURE:
<223> OTHER INFORMATION: hinge fragment 1

<400> SEQUENCE: 6

Asp Lys
1

<210> SEQ ID NO 7
<211> LENGTH: 19
<212> TYPE: PRT
<213> ORGANISM: Artificial Sequence
<220> FEATURE:
<223> OTHER INFORMATION: hinge fragment 2

<400> SEQUENCE: 7

Thr His Thr Cys Pro Pro Cys Pro Ala Pro Glu Leu Leu Gly Gly Pro
1               5                   10                  15

Ser Val Phe
```

DIRECT AFFINITY MEASUREMENT OF HUMAN IgG1 BINDING MULTIMERIC ANTIGENS

CROSS-REFERENCE TO RELATED APPLICATIONS

This application is a continuation of U.S. application Ser. No. 16/003,450, filed on Jun. 8, 2018, which is a continuation of International Patent Application No. PCT/EP2016/079756, having an international filing date of Dec. 5, 2016, the entire contents of which are incorporated herein by reference, and which claims benefit under 35 U.S.C. § 119 to European Patent Application No. 15198556.1, filed on Dec. 9, 2015.

SEQUENCE LISTING

The instant application contains a Sequence Listing which has been submitted electronically in ASCII format and is hereby incorporated by reference in its entirety. Said ASCII copy, created on Oct. 2, 2020 is named P33225-US_1_Sequence_Listing.txt and is 75,296 bytes in size.

FIELD OF THE INVENTION

Herein is reported a fast and easy method for determining affinity constants of human IgG1s binding di- or multimeric antigens using surface plasmon resonance. The method is based on a highly specific and quantitative digestion with lysine-gingipain of *Porphyromonas gingivalis* generating a homogenous pool of intact Fab and Fc-fragments without any over-digestion of the fragments typically associated with other proteolytic enzymes.

BACKGROUND OF THE INVENTION

The quality of a biopharmaceutical product is of decisive importance in addition to its action. Therefore in addition to a detailed investigation of the modes of action, it is absolutely essential to determine the identity, purity and activity of protein-based drugs in order to use them safely as therapeutic agents.

Although mAbs can be successfully analyzed by means of various separation and testing techniques, it has for a long time been difficult to apply and optimize RP-HPLC methods (RP-HPLC, Reversed Phase-High Performance Liquid Chromatography) to separate antibody species. However, various modifications of the antibody are often present simultaneously during the course of a degradation process, which makes it more difficult to analyze the diverse chromatographic and electrophoretic bands. Analysis by means of liquid chromatographic separation methods coupled with high resolution mass spectrometers (LC/MS, liquid chromatography/mass spectrometry) yields information about the exact mass of the various species and thus facilitates the identification of the antibody variants (Dillon, T. M., et al., J. Chromatogr. A, 1053 (2004) 299-305).

Papain, a cysteine protease, cleaves peptide bonds relatively non-specifically after arginine (R), lysine (K), glutamic acid (E), histidine (H), glycine (G) and tyrosine (Y). If the incubation period is sufficiently long, the papain digestion leads to a total hydrolysis. However, antibodies can be cleaved relatively selectively in their hinge region by a limited proteolysis (Lottspeich, F., and Engels, J. W., "Bioanalytik Spektrum Akademischer Verlag" Munich 2nd Edition (2006) 201-214). The cleavage occurs on the N-terminal side of the disulfide bridges which connect the two heavy chains together. The disulfide bridges are retained in this process so that three fragments (2 Fab fragments, 1 Fc fragment) are obtained after the digestion. The two N-terminal fragments are referred to as antigen-binding fragments (Fab, antigen-binding fragment), the C-terminal fragment is referred to as the crystalline fragment (Fc, crystallizing fragment). Each Fab fragment is composed of a complete light chain and the amino-terminal half of the heavy chain. The Fc fragment is composed of the two carboxy-terminal halves of the heavy chains which are still linked together by the disulfide bridge.

In recent years different IgG specific proteases have been identified.

In WO 2015/40125 streptococcal erythrogenic toxin B (SpeB) is reported. It is described as a cysteine protease from *Streptococcus pyogenes*, shown to cleave IgG in the hinge region into two stable monomeric Fab fragments and one Fc fragment. It is further reported that SpeB cleaves the hinge region of IgG between positions 238 and 239 according to the Kabat numbering system (positions 225 and 226 according to EU numbering system).

The cysteine endoprotease IdeS (Immunoglobulin degrading enzyme S) from the human pathogen *Streptococcus pyogenes* which is also referred to as Mac-1 or sib-38, is a cysteine protease that specifically cleaves the heavy chain of antibodies of the immunoglobulin G type (IgG). IgG is hitherto the only known substrate of IdeS (Vincents, B., et al., Biochem. 43 (2004) 15540-15549). IdeS consists of 339 amino acids including a signal peptide comprising 29 amino acids (von Pawel-Rammingen, U., et al., EMBO J. 21 (2002) 1607-1615) where an RGD motif is formed by the amino acids 214 to 216. IdeS cleaves human IgG (class G immunoglobulin) in the hinge region between positions 249 and 250 according to the Kabat numbering system (positions 236 and 237 according to EU numbering system) (Gly-Gly) which are contained in the recognition sequence LLGGP. Human IgG2 is cleaved between the amino acids alanine and glycine in the recognition motif PVAGP. Murine antibodies of the IgG2a and IgG3 type are also cleaved (Vincents, B., et al., Biochem. 43 (2004) 15540-15549).

*Porphyromonas gingivalis* is a major pathogenic factor of the progressive periodontal disease (see e.g. Kadowaki, T., et al., J. Biol. Chem. 269 (1994) 21371-21378). Therefrom different enzymes have been isolated, amongst them gingipains, trypsin-like cysteine proteases.

Kikuchi, Y., et al. reported the determination of concentration and binding affinity of antibody fragments by use of surface plasmon resonance (J. Biosci. Bioeng. 100, (2005) 311-317).

In WO 95/11298 a substantially pure Lys-gingipain complex preparation is provided, wherein Lys-gingipain being characterized as having an apparent molecular mass of 105 kDa as estimated by sodium dodecyl sulfate polyacrylamide gel electrophoresis, where sample is prepared without boiling, said Lys-gingipain having amidolytic and proteolytic activity for cleavage after lysine residues and having no amidolytic and/or proteolytic activity for cleavage after arginine residues, wherein the amidolytic and/or proteolytic activity is inhibited by TLCK, cysteine protease group-specific inhibitors including iodoacetamide and iodoacetic acid, wherein the amidolytic and/or proteolytic activity of said Lys-gingipain is not sensitive to inhibition by leupeptin, antipain, trans-epoxysuccinyl-L-leucylamido-(4-guanidino) butane, serine protease group-specific inhibitors including diisopropylfluorophosphate and phenylmethyl sulfonylfluoride, and antibodies specific for the Lys-gingipain protein complex and its catalytic component, methods for preparation.

Inagaki, S., et al. reported about antibody responses of periodontitis patients to gingipains of *Porphyromonas gingivalis* (J. Periodont. 74 (2003) 1432-1439).

Nguyen, H., et al. reported that surface plasmon resonance is a versatile technique for biosensor applications (Sensors 15 (2015) 10481-10510).

SUMMARY OF THE INVENTION

Herein is reported a method for the determination of the binding affinity of a full length antibody of the human IgG1 subclass to its antigen using the fragment antigen binding (Fab) generated thereof in a surface plasmon resonance method whereby the Fabs are generated enzymatically by incubation with lysine-gingipain of *Porphyromonas gingivalis* and the reaction mixture is directly used for affinity determination without intermediate purification.

One aspect as reported herein is a method for determining the binding affinity of the binding sites of a bivalent full length antibody of the human IgG1 subclass to its homo-multimeric antigen comprising the following steps:
 incubating a mixture comprising the antibody and a polypeptide that is derived from lysine-gingipain of *Porphyromonas gingivalis* under conditions and for a time sufficient to cleave the antibody into Fabs and Fc-region, and
 determining the binding affinity of the Fabs of the antibody for their antigen using a surface plasmon resonance method by directly applying the incubated reaction mixture obtained in the previous step in the surface plasmon resonance method
 and
 thereby determining the binding affinity of the binding sites of the bivalent full length antibody of the human IgG1 subclass.

One aspect as reported herein is a method for determining the binding affinity of the binding sites of a bivalent full length antibody of the human IgG1 subclass to a homo-multimeric antigen comprising the following steps:
 incubating a mixture comprising the antibody and lysine-gingipain of *Porphyromonas gingivalis* or a enzymatically active fragment thereof at a pH of (from pH) 7.5 to (pH) 8.5, in the presence of a reducing agent, at a temperature of (from) 30° C. to 42° C., for a time of (from) 10 min. to 240 min. to cleave the antibody into Fabs and Fc-region, and
 determining the binding affinity of the Fabs of the antibody for its antigen using surface plasmon resonance by directly applying the incubated reaction mixture obtained in the previous step in the surface plasmon resonance method
 and
 thereby determining the binding affinity of the binding sites of the bivalent full length antibody of the human IgG1 subclass.

In one embodiment the method comprises the following steps:
 incubating a mixture comprising the antibody and a polypeptide that is derived from lysine-gingipain of *Porphyromonas gingivalis* at a pH of (from pH) 7.5 to (pH) 8.5, in the presence of a reducing agent, at a temperature of (from) 30° C. to 42° C., for time of (from) 10 min. to 240 min. to cleave the antibody into Fabs and Fc-region, and
 determining the binding affinity of the Fabs of the antibody for their antigen using a surface plasmon resonance method by directly applying the incubated reaction mixture obtained in the previous step in the surface plasmon resonance method
 and
 thereby determining the binding affinity of the binding sites of the bivalent full length antibody of the human IgG1 subclass.

In one embodiment the polypeptide that is derived from lysine-gingipain of *Porphyromonas gingivalis* is the lysine-gingipain of *Porphyromonas gingivalis*. In one embodiment the polypeptide that is derived from lysine-gingipain of *Porphyromonas gingivalis* comprises the amino acid sequence of SEQ ID NO: 02 or SEQ ID NO: 03 or SEQ ID NO: 04 or a functional variant thereof. In one embodiment the lysine-gingipain of *Porphyromonas gingivalis* has the amino acid sequence of SEQ ID NO: 02 or SEQ ID NO: 03 or SEQ ID NO: 04 or is a functional variant thereof. In one embodiment the polypeptide that is derived from lysine-gingipain of *Porphyromonas gingivalis* has an amino acid sequence that comprises at least residues 230 to 739 of SEQ ID NO: 01.

In one embodiment the reducing agent is selected from the group consisting of 2-mercaptoethanol, cysteine, and dithiothreitol. In one embodiment the reducing agent is cysteine. In one embodiment the reducing agent is cysteine at a concentration of (from) 0.5 mM to 10 mM. In one embodiment the reducing agent is cysteine at a concentration of about 2 mM.

In one embodiment the pH value is about pH 8.

In one embodiment the temperature is of (from) 35° C. to 38° C. In one embodiment the temperature is about 37° C.

In one embodiment the incubating is for a time of (from) 30 min. to 120 min. In one embodiment the incubating is for a time of about 60 min.

In one embodiment the antibody comprises in the Fc-region the mutations P329G, L234A and L235A in both heavy chain polypeptides.

One aspect as reported herein is a method for selecting an antibody (specifically binding to a homo-multimeric antigen) comprising the following steps:
 providing a plurality of bivalent full length antibodies of the human IgG1 subclass binding to the same antigen,
 determining the binding affinity of each of the antibodies of the plurality of antibodies to its homo-multimeric antigen with a method according to any one of claims 1 to 11, and
 selecting one or more antibodies based on the binding affinity determined in the previous step.

DETAILED DESCRIPTION OF THE INVENTION

Definitions

As used herein, the amino acid positions of all constant regions and domains of the heavy and light chain are numbered according to the Kabat numbering system described in Kabat, et al., Sequences of Proteins of Immunological Interest, 5th ed., Public Health Service, National Institutes of Health, Bethesda, Md. (1991) and is referred to as "numbering according to Kabat" herein. Specifically, the Kabat numbering system (see pages 647-660) of Kabat, et al., Sequences of Proteins of Immunological Interest, 5th ed., Public Health Service, National Institutes of Health, Bethesda, Md. (1991) is used for the light chain constant domain CL of kappa and lambda isotype, and the Kabat EU index numbering system (see pages 661-723) is used for the constant heavy chain domains (CH1, Hinge, CH2 and CH3, which is herein further clarified by referring to "numbering according to Kabat EU index" in this case).

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

The term "about" denotes a range of +/−20% of the thereafter following numerical value. In one embodiment the term about denotes a range of +/−10% of the thereafter following numerical value. In one embodiment the term about denotes a range of +/−5% of the thereafter following numerical value.

The term "lysine-gingipain of *Porphyromonas gingivalis*" denotes a polypeptide that specifically cleaves human IgG1 and IgG3 subclass heavy chains between positions 238 and 239 according to the Kabat numbering system (positions 225 and 226 according to EU numbering system), i.e. the hinge region amino acid sequence DKTHTCPPCPA-PELLGGPSVF (SEQ ID NO: 05) is cleaved after the second amino acid residue resulting in the fragments DK (SEQ ID NO: 06) and THTCPPCPAPELLGGPSVF (SEQ ID NO: 07). In one embodiment the polypeptide, i.e. the lysine-gingipain of *Porphyromonas gingivalis*, comprises the amino acid sequence of SEQ ID NO: 02 or SEQ ID NO: 03 or SEQ ID NO: 04 or a functional variant thereof. In one embodiment the polypeptide, i.e. the lysine-gingipain of *Porphyromonas gingivalis*, has an amino acid sequence that comprises at least residues 230 to 739 of SEQ ID NO: 01. The "lysine-gingipain of *Porphyromonas gingivalis*" has the EC number 3.4.22.47 and is also denoted as gingipain K, KGP, Lys-gingipain, PrtP proteinase, lysine-specific cysteine protease, lysine-specific gingipain, lysine-specific gingipain K, or lysine-specific gingipain proteinase. The full length amino acid sequence of an exemplary lysine-gingipain of *Porphyromonas gingivalis* is denoted in SEQ ID NO: 01. This polypeptide is an endopeptidase with strict specificity for lysyl bonds. The enzymatic activity of the polypeptide is activated by the addition of about 30 2-mercaptoethanol, about 50 mM cysteine, about 30 mM dithiothreitol, about 2 mM EDTA, about 2 mM EGTA or glutathione. It is active in the pH range from pH 6.5 to pH 9.5, with a pH of from about pH 7.5 to about pH 8.5 (preferably about pH 8.0) being suitable for the hydrolysis of immunoglobulins. In an exemplary IgG degradation method the following conditions are used: IgG (final concentration 15 μM), KGP (final concentration 10 nM active protease), Tris buffer (0.1 mol/L, pH 8.0), EDTA (final concentration 1 mM), L-cysteine (final concentration 2 mM), 37° C. Human IgGs are cleaved once but if the glycostructures are removed a second cleavage might occur. The enzymatic cleavage can be negatively affected if chaotropic reagents and/or detergents are present. Thus, in one embodiment the method is performed in the absence of chaotropic reagents and/or detergents from all solutions used in the method.

The term "full-length antibody" denotes an antibody which comprises two so called light immunoglobulin chain polypeptides (light chain) and two so called heavy immunoglobulin chain polypeptides (heavy chain). Each of the heavy and light immunoglobulin chain polypeptides of a full-length antibody contains a variable domain (variable region) (generally the amino terminal portion of the polypeptide chain) comprising binding regions that are able to interact with an antigen. Each of the heavy and light immunoglobulin chain polypeptides of full-length antibody comprises a constant region (generally the carboxyl terminal portion). The constant region of the heavy chain mediates the binding of the antibody i) to cells bearing a Fc gamma receptor (FcγR), such as phagocytic cells, or ii) to cells bearing the neonatal Fc receptor (FcRn) also known as Brambell receptor. It also mediates the binding to some factors including factors of the classical complement system such as component (Clq). The variable domain of an antibody's light or heavy chain in turn comprises different segments, i.e. four framework regions (FR) and three hypervariable regions (CDR).

The term "monoclonal antibody" as used herein refers to an antibody obtained from a population of substantially homogeneous antibodies, i.e. the individual antibodies comprising the population are identical except for possible naturally occurring mutations that may be present in minor amounts. Monoclonal are highly specific, being directed against a single antigenic site. Furthermore, in contrast to polyclonal antibody preparations, which include different antibodies directed against different antigenic sites (determinants or epitopes), each monoclonal antibody is directed against a single antigenic site on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies and is not to be construed as requiring production of the antibody by any particular method.

The "Fc-region" of an antibody is not involved directly in binding to the antibody's antigen, but exhibits various effector functions. Depending on the amino acid sequence of the constant region of the heavy chains, antibodies (immunoglobulins) are divided in the classes: IgA, IgD, IgE, IgG, and IgM. Some of these classes are further divided into subclasses (isotypes), i.e. IgG in IgG1, IgG2, IgG3, and IgG4, or IgA in IgA1 and IgA2. According to the immunoglobulin class to which an antibody belongs are the heavy chain constant regions of immunoglobulins are called ☐☐☐IgA), ☐(IgD), ☐ (IgE)☐☐☐(IgG), and ☐ (IgM), respectively. The antibodies according to the invention belong preferably to the IgG class. An "Fc-region of an antibody" is a term well known to the skilled artisan and defined on basis of the papain cleavage of antibodies.

Affinity Determination:

Normally antibodies, such as full length antibodies of the IgG class, are bivalent. Thus, when determining the affinity it should be a "true" affinity avoiding the avidity effect of the bivalent binder. To determine the affinity and binding kinetics of antibodies binding bi- or multivalent targets it is therefore necessary to turn the bivalent antibodies into monovalent binding entities like fragment antigen-binding (Fab) units.

Currently methods for the determination of the affinity of bivalent antibodies are two step methods:
 1: cleavage of the antibody to be analyzed to generate monovalent binding entities, and
 2: purification of the reaction mixture of 1.

Alternatively it is possible to re-clone and express the Fab fragment for which even more time and labor are required as for the approach outlined above.

Generation of IgG-Fragments:

Often, Fab fragments are generated by partial proteolytic digestions of IgGs with unspecific proteases like papain or pepsin, which cleave above or below the hinge region, respectively. The fragments contain the disulphide bonds that join the heavy chains, but the cleavage is below the site of the disulphide bond between the light chain and heavy chain (Porter, 1959; Nisonoff et al., 1960; Akita and Nakai, 1993, Andrew and Titus, 2003; Mage, 1987; Zhao et al., 2009; Andrew, S. M. and J. A. Titus. 2003).

IgGs digested with pepsin results in F(ab')2 fragments that are subsequently mildly reduced to give Fab' fragments. Most likely the hinge region is more susceptible to the attack of proteases as it is exposed and flexible. Subsequently, the fragments are then purified from the digestion mix.

However, lack of reproducibility, uncut IgG and over-digestion is often a problem.

With papain digestion, e.g., it is difficult to obtain homogeneous Fabs (Parham, 1983; 1986; Mage, 1987). Immobilized papain products (e.g. papain agarose resins; see e.g. Tischer, W., and V. Kasche, 1999; Luo, Q., et al. 2002) allow better control of the digestion reaction and efficient removal of the Fab and Fc fragments from the crude protease digest; nevertheless purification is still required.

Another approach to obtain monomeric antigen-binding fragments include the generation of F(ab')2 fragments by digestion with Immunoglobulin G-degrading enzyme of *S. pyogenes* (IdeS) and mild reduction with 2-mercaptoethylamine (2-MEA) to generate Fab' fragments (von Pawel-Rammingen, U., et al. 2002+2003; Ishikawa, E. and S. Yoshitake, 1980; DeSilva, B. S., et al., 1995).

The two antigen-binding domains of an antibody of the IgG class can also be obtained by reducing the IgG to two half-IgGs (rIgG; see e.g. Billah, M. M., et al., 2010). It is the product of selectively reducing just the hinge-region disulphide bonds which are the most accessible and easiest to reduce, especially with a mild reducing agents like 2-MEA.

Finally, a Fab can also be obtained by recombinant expression of the light chain and the heavy chain Fd-fragment (VH—CH1) (Zhao et al., 2009). This is however time consuming and laborious if several different Fabs are needed for e.g. a comparison.

A limited digestion using the endoproteinase Lys-C in a 40 min digestion of hIgG1's to analyze the chain assembly by mass spectrometry has been reported in PCT/EP2015/057164. Using this procedure Lys-C exclusively cuts once above the hinge region generating Fab and Fc-fragments.

A protease that cleaves selectively in the upper hinge region of antibodies of the IgGs class is streptococcal erythrogenic toxin B (SpeB) from *Streptococcus pyogenes* (von Pawel-Rammingen, U., et al. 2002). This protease requires reducing agent like DTT or TCEP in the range of 1-5 mM for activity (Persson, H., et al., 2013; www(dot)genovis(dot)com/fabulous) resulting in the concomitant reduction of the interchain thiols of the digested antibody.

IgG-specific proteases and their cleavage sites are shown in the following Table (see also Brerski, R. J. and Jordan, R. E., mAbs 2 (2010) 212-220).

| protease | specificity | recognition sequence | fragments |
|---|---|---|---|
| plasmin | | DK↓THTCPPCPAPELLGGPSVF (SEQ ID NO: 05) | 2xFab 1xFc |
| lysine-gingipain of porphyromonas gingivalis | human IgG1 and IgG3, IgA | DK↓THTCPPCPAPELLGGPSVF | 2xFab 1xFc |
| human neutrophil elastase | | DKT↓HTCPPCPAPELLGGPSVF | 2xFab 1xFc |
| papain | IgG, specific only in limited proteolysis | DKTH↓TCPPCPAPELLGGPSVF | 2xFab 1xFc |
| streptococcal erythrogenic toxin B (SpeB) from *S. pyogenes* | | DKTHT↓CPPCPAPELLGGPSVF | 2xFd 2xLC 1xFc |
| glutamyl endopeptidase I from *S. aureus*, Cathepsin G | | DKTHTCPPCPAPE↓LLGGPSVF | 1xF(ab')2 |
| pepsin | IgG1 > IgG2 | DKTHTCPPCPAPEL↓LGGPSVF | 1xF(ab')2 multiple HC-Fc fragments |
| Immunoglobulin G-degrading enzyme of *S. pyogenes* (IdeS) | | DKTHTCPPCPAPELLG↓GPSVF | 1xF(ab')2 2xHC-Fc |

The *P. gingivalis* proteases have been studied since more than 30 years. They have been identified as cysteine-proteinases requiring the presence of reducing agents for activity. One of them is the cysteine protease gingipain K (EC. 3.4.22.47).

Scott et al. purified lysine-gingipain of *Porphyromonas gingivalis* (KGP) back in 1993 (Scott, C. F., et al., J. Biol. Chem. 268 (1993) 7935-7942).

Scott et al. identified cysteine, dithiothreitol, glutathione and 2-mercaptoethanol to be suitable reducing agents for the activation of KGP.

KGP cleaves peptides with Lys in the P1 position, and the residue at P2 appears to be less important. However, if P2 is occupied by Lys or Arg, hydrolysis appears to be blocked. KGP is capable of hydrolyzing protein substrates such as BSA, casein, hemoglobin, acid-soluble human placental type I collagen, human IgG, and IgA (Curtis, M. A., et al., Crit. Rev. Oral Biol. Med. 12 (2001) 192-216).

The amino acid sequence of lysine-gingipain of *Porphyromonas gingivalis* including an identification of the respective domains was reported by Okamoto, K., et al. (J. Biochem. 120 (1996) 398-406). The kgp gene was reported and deposited by Slakeski, N., et al. under accession number U75366 and AAB60809.1 (Oral Microbiol. Immunol. 14 (1999) 92-97). Several C-terminally truncated but active forms have been identified. It has been found that for the C-terminally truncated proteins KGP($\Delta$1292-1732), KGP ($\Delta$1157-1732), KGP($\Delta$738-1732), KGP($\Delta$681-1732) and KGP($\Delta$602-1732) enzymatic activity was only barely measurable for the last two mutants (see e.g. Sztukowska, M., et al., Mol. Microbiol. 54 (2004) 1393-1408).

KGP has a narrow specificity for synthetic substrates, limited to peptide bonds containing arginine and lysine residues, respectively, but they can nevertheless degrade immunoglobulins G and A in a limited degradation manner (Yamamoto, K., et al., In: Proteases: new Perspectives (1999), V. Turk (ed.), Birkhäauser Verlag Basel (CH), 175-184; Yamamoto, K., et al., In: N Katunuma, H Kido, H Fritz, J Travis (Eds): Medical Aspects of Proteases and Protease Inhibitors. 105 Press, Amsterdam, 139-149; Kadowaki, T., et al., J. Biol. Chem. 269 (1994) 21371-21378; Abe, N., et al., J. Biochem. 123 (1998) 305-312).

Comparative properties of envelope-associated arginine-gingipains (RGP) and lysine-gingipain (KGP) of *Porphyromonas gingivalis* have been reported in 1998 by Fujimura et al. (Microbiol. Lett. 163 (1998) 173-179). The enzymes were commonly activated by reducing reagents such as mercaptoethanol, dithiothreitol and cysteine. RGP-B was activated markedly by glycyl-glycine and KGP was activated significantly by EDTA and EGTA. The hydrolytic activities of RGPs and KGP to chromogenic synthetic substrates were limited to the compounds with arginine and lysine in the P-1 positions, respectively. When IgG was treated with the three enzymes separately, it was demonstrated that two new fragments of 34 kDa and 15 kDa (SDS under reducing conditions) were generated in each reaction product. The optimum pH for the activity of KGP was found to be 7.5. Thiol reagents activated both RGPs and KGP, whereas dithiothreitol was the best activator of KGP (at 20-30 mM), followed by mercaptoethanol (at 20-30 mM) and cysteine (at more than 1.5 mM but less than 10 mM). KGP split only X-Y-Lys-pNA.

Vincents, B., et al. reported that gingipain K of *Porphyromonas gingivalis* can hydrolyze subclass 1 and 3 of human IgG, whereby the heavy chain of IgG1 was cleaved at a single site within the hinge region, generating Fab and Fc fragments and that IgG3 was also cleaved within the heavy chain, but at several sites around the CH2 region (FASEB J., 25 (2011) 3741-3750). Cleavage of IgG2 is not mediated by KGP (Guentsch, A., et al., J. Periodont. res. 48 (2013) 458-465).

An high-resolution crystal structure of KGP active site was reported by de Diego, I., et al. suggesting that catalysis may require a catalytic triad, Cys477-His444-Asp388, rather than the cysteine-histidine dyad normally found in cysteine peptidases (J. Biol. Chem. 289 (2014) 32291-32302).

Different antibody fragments are described in the following:
the F(ab')2 fragment:
the F(ab')2 fragment has a molecular weight of about 110 kDa and comprises the two antigen-binding site of a full length antibody of the IgG class connected via the hinge-region disulfide bonds; it is void of most, but not all, of the Fc-region
Fab' fragment:
the Fab' fragment has a molecular weight of about 55 kDa; it can be formed by the reduction of the hinge-region disulfide bonds of a F(ab')2 fragment; the Fab' fragment comprises a free sulfhydryl group; as it is derived from F(ab')2 it may contain a small portion of the Fc.-region
fragment antigen binding—Fab:
the Fab has a molecular weight of about 50 kDa; it is a monovalent binding fragment that can be obtained from antibodies of the IgG and IgM class; it comprises the VH and CH1 domains of the heavy chain and a complete light chain both linked by an intramolecular disulfide bond
Fv fragment:
the Fv fragment has a molecular weight of about 25 kDa; it is the smallest antibody fragment that contains a complete antigen-binding site (VH domain and VL domain); the VH and VL domains of the Fv fragment are held together by non-covalent interactions
"rIgG" fragment:
the "rIgG" fragment denotes a half-antibody that is obtained by reducing just the hinge-region disulfide bonds of a full length antibody (e.g. using 2-MEA); it has a molecular weight of about 75 kDa
fragment crystallizable—Fc-fragment:
the Fc-fragment has a molecular weight of about 50 kDa; it comprises the CH2 and CH3 domains of the heavy chain of a full length antibody and part of the hinge region; the two chains are held together by one or more disulfide bonds (in the hinge region); the Fc-fragment cannot bind the antigen, but it is responsible for the effector functions of the full length antibody.

The Method as Reported Herein:

Different from antibodies binding monomeric antigens, it is not feasible to determine the affinity without the influence of avidity of antibodies binding di- or multimeric antigens, for example by surface plasmon resonance (SPR).

Affinity describes the strength of a single interaction between antibody and its antigen. A bivalent antibody of the IgG class has two antigen-binding sites, and the avidity is commonly applied to antibody interactions in which multiple antigen-binding sites simultaneously interact with the target antigen, often in multimeric structures. The avidity of an antibody refers to the accumulated strength of multiple affinities. Avidity is commonly obtained regarding interactions in which multiple antigen-binding sites, often in multimeric structures, are involved. To determine the affinity of antibodies it is necessary to convert the bivalent antibodies into monovalent binding entities like antigen-binding fragments (Fab).

The determination of affinity constants of antibodies targeting di- or multimeric antigens by SPR therefore necessitates the generation of monomeric antigen-binding fragments, such as e.g. Fabs. The generation of Fabs is however laborious. Often, Fabs are generated by partial proteolytic digestions with papain.

Herein is reported a fast and easy method for the generation of Fabs from full length antibodies of the IgG1 subclass. It has been found that the lysine-gingipain of *Porphyromonas gingivalis* can be used for the generation of Fabs from full length antibodies of the IgG1 subclass as with this enzyme a highly specific and quantitative protease digestion generating a homogenous pool of intact Fab and Fc-fragments without any over-digestion typically associated with other proteolytic enzymes can be achieved and the reaction mixture can directly, i.e. without any intermediate purification, be applied to a surface plasmon resonance chip.

In more detail this is done by in solution digestion and direct kinetic affinity determination of the Fab fragment by SPR without any prior purification or cleaning step. The complete digestion by the lysine-gingipain of *Porphyromonas gingivalis* of human IgG1s was verified by ESI-QTOF-MS.

The method as reported herein can be used for the determination of kinetic rate constants of human or humanized antibodies, e.g. of the subclass IgG1 or comprising an Fc-region derived from the human subclass IgG1, specifically binding to di- or multimeric antigens using a surface plasmon resonance method. The method comprises in one embodiment the following steps: 1) incubating the antibody with the lysine-gingipain of *Porphyromonas gingivalis* to cleave it completely generating a homogenous pool of Fabs and Fc-fragments, and 2) determining the binding affinity of the Fab in the digestion mixture by surface plasmon resonance (SPR). Direct SPR on the digestion mixture allows precise kinetic characterization of the Fab fragment without any prior purification.

It has been found that the affinity constants determined by SPR of Fabs of antibodies of the IgG1 subclass obtained by digesting with the lysine-gingipain of *Porphyromonas gingivalis* without subsequent purification correspond to affinity constants of Fabs obtained by recombinant expression, or by digesting with papain and subsequent purification prior to SPR measurement.

One aspect as reported herein is a method for determining the binding affinity of the binding sites of a bivalent full length antibody of the human IgG1 subclass to its antigen comprising the following steps:
  incubating a mixture comprising the antibody and a polypeptide that is derived from lysine-gingipain of *Porphyromonas gingivalis* under conditions and for a time sufficient to cleave the antibody into Fabs and Fc-region, and
  determining the binding affinity of the Fabs of the antibody for their antigen using a surface plasmon resonance method by directly applying the incubated reaction mixture obtained in the previous step in the surface plasmon resonance method
  and
  thereby determining the binding affinity of the binding sites of the bivalent full length antibody of the human IgG1 subclass.

In one embodiment the method comprises the following steps:
  incubating a mixture comprising the antibody and a polypeptide that is derived from lysine-gingipain of *Porphyromonas gingivalis* at a pH of from pH 7.5 to pH 8.5, in the presence of a reducing agent, at a temperature of from 30° C. to 42° C., for time of from 10 min. to 240 min. to cleave the antibody into Fabs and Fc-region, and
  determining the binding affinity of the Fabs of the antibody for their antigen using a surface plasmon resonance method by directly applying the incubated reaction mixture obtained in the previous step in the surface plasmon resonance method
  and
  thereby determining the binding affinity of the binding sites of the bivalent full length antibody of the human IgG1 subclass.

In one embodiment the polypeptide that is derived from lysine-gingipain of *Porphyromonas gingivalis* is the lysine-gingipain of *Porphyromonas gingivalis*. In one embodiment the polypeptide that is derived from lysine-gingipain of *Porphyromonas gingivalis* comprises the amino acid sequence of SEQ ID NO: 02 or SEQ ID NO: 03 or SEQ ID NO: 04 or a functional variant thereof. In one embodiment the polypeptide that is derived from lysine-gingipain of *Porphyromonas gingivalis* has an amino acid sequence that comprises at least residues 230 to 739 of SEQ ID NO: 01.

In one embodiment the reducing agent is selected from the group consisting of 2-mercaptoethanol, cysteine, and dithiothreitol. In one embodiment the reducing agent is cysteine. In one embodiment the reducing agent is cysteine at a concentration of from 0.5 mM to 10 mM. In one embodiment the reducing agent is cysteine at a concentration of about 2 mM.

In one embodiment the pH value is about pH 8.

In one embodiment the temperature is of from 35° C. to 38° C. In one embodiment the temperature is about 37° C.

In one embodiment the incubating is for a time of from 30 min. to 120 min. In one embodiment the incubating is for a time of about 60 min.

In one embodiment the antibody comprises in the Fc-region the mutations P329G, L234A and L235A in both heavy chain polypeptides.

In one embodiment the antigen is multimeric antigen. In one embodiment the antigen is a homo-multimeric antigen. In one embodiment the antigen is selected from the group consisting of vascular endothelial growth factor A (VEGF-A), carcinoembryonic antigen (CEA), angiopoietin-2 (ANG2), and fibroblast activation protein (FAP).

One aspect as reported herein is a method for selecting an antibody comprising the following steps:
  providing a plurality of bivalent full length antibodies of the human IgG1 subclass binding to the same antigen,
  determining the binding affinity of each of the antibodies of the plurality of antibodies to its antigen with a method according to any one of claims 1 to 11, and
  selecting one or more antibodies based on the binding affinity determined in the previous step.

The method as reported herein allows for a fast determination of the affinity of a bivalent full length antibody for its antigen without the requirements to recombinantly produce a single binding site version of the antibody. With the method as reported herein the determination of the biding affinity of the bivalent full length antibody for its antigen is possible without the need for an intermediate purification of the reaction mixture that has been used for the generation of the Fabs of the bivalent full length antibody.

The method as reported herein has been exemplified in the following with the antibody bevacizumab. Bevacizumab is a humanized anti-VEGF antibody of the human IgG1 subclass. The therapeutic antibody bevacizumab binds a dimeric antigen, i.e. VEGF-A (dimeric is a form of homo-multimeric).

The quality of the bevacizumab Fabs and digests was analyzed by UHR ESI-QTOF mass spectrometry. The deconvoluted mass spectra of the purified Fab following a papain digest, and a purified recombinant Fab provided proof for the high quality of both materials as only the masses of the Fab fragments could be detected.

In more detail, complete digestion of bevacizumab by the lysine-gingipain of Porphyromonas gingivalis was verified by electrospray ionization mass spectrometry after desalting of the reaction mixture using a size exclusion chromatography. No fragmentation or side products could be identified in the MS spectra.

For comparison bevacizumab has been digested using the enzyme papain. Form the MS spectra it can be seen that papain is not suitable for functional assessment due to unspecific fragmentation of the antibody and loss of function.

The respective MS-spectra are shown in FIG. 1 (one hour digestion with the lysine-gingipain of Porphyromonas gingivalis), FIG. 2 (1.5 hours digestion with papain), and FIG. 3 (2 hour digestion with papain). It can be seen that no antibody fragmentation beside the single cleavage in the hinge region occurred when the lysine-gingipain of Porphyromonas gingivalis was used.

In more detail, the quality of the recombinant bevacizumab Fab and papain and lysine-gingipain of Porphyromonas gingivalis digests were analyzed by UHR ESI-QTOF mass spectrometry. The deconvoluted mass spectra of the purified Fab following a papain digest, and a purified recombinant Fab revealed the high quality of both materials as only the masses of the intact Fab 48208 Da (theoretical average mass: 48208 Da) and 47726 Da (theoretical average mass: 47726), respectively, could be detected. The evaluation of the mass spectrum of bevacizumab digested with papain revealed not only the presence of the 48207 Da Fab (theoretical average mass: 48208 Da) and the Fc-fragments (multiple masses present due to heterogeneity of the Fc N-glycan's). In addition, unassignable fragments corresponding to the masses x:23422 Da and 23453 Da, y:34587 Da, and z:47607 Da were detected in the papain digest. In contrast the deconvoluted mass spectrum of bevacizumab digested with the lysine-gingipain of Porphyromonas gingivalis demonstrated only the presence of the 47969 Da Fab (theoretical average mass: 47970 Da) and the Fc-fragment (multiple masses present due to the Fc N-glycan's). The digestion with the lysine-gingipain of Porphyromonas gingivalis was complete without any undigested or single cut IgG (IgG without one Fab) detectable by mass spectrometry. Nor could any unspecific digestion, over-digestion, or further degradation of the fragments be detected in the crude digestion mixture of the lysine-gingipain of Porphyromonas gingivalis digest.

The method as reported herein was performed with different bevacizumab-derived samples:
1) full length bivalent antibody
2) recombinantly produced Fab
3) Fab produced with a method as reported herein (without intermediate purification) (determined directly after the incubation and after 24 hours additional incubation in the presence of functional lysine-gingipain of Porphyromonas gingivalis)
4) Fab produced with papain (without termination of the reaction and without intermediate purification)
5) Fab produced with papain (with termination of the reaction, without intermediate purification)
6) Fab produced with papain (with intermediate purification)

In order to compare the affinities of the different produced Fabs of bevacizumab the binding affinities of bevacizumab digested with the lysine-gingipain of Porphyromonas gingivalis without purification of the Fab and the binding affinities of a recombinant transiently expressed bevacizumab Fab, a purified Fab following a papain digest were determined.

For determining the affinities a murine anti-His-tag antibody was immobilized and the dimeric VEGF-A conjugated to a His-tag was captured on the sensor chip surface. Afterwards, the analytes binding to VEGF-A were injected and flew over the surface. The derived sensorgrams were fitted to a 1:1 Langmuir binding model and used to determine the association rate constants ka, the dissociation rate constants kd, and the binding constants KD. Generally, the rate and binding constants for the Fab fragments were all very similar (see Table below). The binding constant of the Fab in the lysine-gingipain of Porphyromonas gingivalis digestion mixture was found to be 1.1 nM, and those of the recombinant Fab and the purified Fab after digestion with papain were determined to 0.8 and 1.0 nM, respectively. The KD of the full length bivalent antibody was determined to be 0.18 nM demonstrating the avid binding to the dimeric VEGF-A. But when the papain digestion mixture was applied to the immobilized chip surface, we did not observe binding to the captured dimeric VEGF-A. Consequently, no binding constant could be determined for the papain digestion mixture. It has been found that the VEGF-A surface was damaged after applying the papain containing samples as it could not be used anymore.

The results are presented in the following Table.

| sample | ka [1/Ms] | kd [1/s] | KD [nM] |
|---|---|---|---|
| full length bevacizumab (avidity) | 1.61E+05 | 2.96E−05 | 0.18 |
| recombinant bevacizumab Fab (affinity) | 9.03E+04 | 7.37E−05 | 0.8 |
| bevacizumab digested lysine-gingipain of porphyromonas gingivalis, without purification (without additional incubation) | 5.18E+04 | 5.83E−05 | 1.1 |
| bevacizumab digested with papain (without termination of the reaction and without intermediate purification) | could not be determined as no binding signal was observed | | |
| bevacizumab digested with papain (with termination of the reaction, without intermediate purification) | could not be determined as no binding signal was observed | | |
| bevacizumab digested with papain (with intermediate purification) | 7.95E+04 | 8.02E−05 | 1.0 |

It can be seen that as the lysine-gingipain of Porphyromonas gingivalis is specific for human IgG1, it does not destroy the immobilized chip surface. In contrast thereto no binding was observed after the not purified papain digestion reaction mixture was applied to the immobilized chip surface. The VEGF surface could not be used any more after applying the papain containing sample as it has been damaged by the presence of papain.

The respective SPR diagrams are shown in FIG. 4A to 4D.

Storage of the lysine-gingipain of Porphyromonas gingivalis-digested bevacizumab and repeated affinity determinations by SPR allowed to conclude the digests to be stable at 4° C. for at least 24 and 48 hours, respectively, i.e. no further digestion or fragmentation occurred.

Beside the use of lysine-gingipain of *Porphyromonas gingivalis* for the determination of affinities of human IgG1 s binding di- or multimeric antigens, the protease can also be used in cases where IgG1s binding monomeric antigens are difficult to immobilize on the SPR metal surface.

In addition, the lysine-gingipain of *Porphyromonas gingivalis* will be very beneficial for the structural analysis of the Fab fragments and structure-function relationships of human IgG1-antigen binding at atomic resolution, e.g., by X-ray crystallography. Compared with IgGs, Fab fragments are more amenable to crystallization.

Recombinant Methods:

Antibodies may be produced using recombinant methods and compositions, e.g., as described in U.S. Pat. No. 4,816, 567. In one embodiment, isolated nucleic acid encoding an antibody as described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of producing an antibody as reported herein is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, K. A., In: Methods in Molecular Biology, Vol. 248, Lo, B. K. C. (ed.), Humana Press, Totowa, N.J. (2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, T. U., Nat. Biotech. 22 (2004) 1409-1414; and Li, H. et al., Nat. Biotech. 24 (2006) 210-215.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham, F. L. et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather, J. P. et al., Annals N.Y. Acad. Sci. 383 (1982) 44-68; MRC 5 cells; and FS4 cells. Other useful mammalian host cell lines include Chinese hamster ovary (CHO) cells, including DHFR-CHO cells (Urlaub, G. et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A M., Methods in Molecular Biology, Vol. 248, Lo, B. K. C. (ed.), Humana Press, Totowa, N.J. (2004), pp. 255-268.

General chromatographic methods are known to a person skilled in the art e.g. Chromatography, 5th edition, Part A: Fundamentals and Techniques, Heftmann, E. (ed.); Elsevier Science Publishing Company, New York, (1992); Advanced Chromatographic and Electromigration Methods in Biosciences, Deyl, Z. (ed.), Elsevier Science BV, Amsterdam, The Netherlands, (1998); Chromatography Today, Poole, D. F., and Poole, S. K., Elsevier Science Publishing Company, New York, (1991); Scopes, Protein Purification: Principles and Practice (1982); Sambrook, J., et al. (ed.), Molecular Cloning: A Laboratory Manual, Second Edition, Cold Spring Harbor Laboratory Press, Cold Spring Harbor, N.Y., 1989; or Current Protocols in Molecular Biology, Ausubel, F. M., et al. (eds.), John Wiley & Sons, Inc., New York.

CITATIONS

Andrew S. M., Titus J. A., 2003, Fragmentation of immunoglobulin G. Curr Protoc Cell Biol. Unit 16.4. (Chapter 16).

Mage, E. L. M., 1987, Preparation of Fab and F(ab') fragments from monoclonal antibodies, p. 79-97. In: L. B. Schook (Ed.), Monoclonal antibody production techniques and applications, Marcel Dekker Inc., New York.

Parham, P., J Immunol. 131 (1983) 2895-2902.

Parham, P., 1986, Preparation and purification of active fragments from mouse monoclonal antibodies, p. 14.1-14.23. In: D. M. Weir (Ed.), Handbook of Experimental Immunology, 4th Ed. Blackwell Scientific Publications, Oxford.

Porter, R. R., Biochem J. 73 (1959) 119-126.
Nisonoff, A., et al., Arch. Biochem. Biophys. 89 (1960) 230-244.
Zhao, Y. L., et al., Protein Expr. Purif. 67 (2009) 182-189.
Akita, E. M., and S. Nakai, J. Immunol. Methods 162 (1993) 155-164.
Tischer, W. and V. Kasche, Trends Biotechnol. 17 (1999) 326-335.
Luo, Q., et al., J. Chrom. 776 (2002) 139-147.
von Pawel-Rammingen, U., et al., EMBO J. 21 (2002) 1607-1615.
von Pawel-Rammingen, U. and L. Björck, Curr. Opin. Microbiol. 6 (2003) 50-55.
Ishikawa, E. and S. Yoshitake, J. Immunol. Methods 38 (1980) 117-123.
DeSilva, B. S. and G. S. Wilson, G. S., J. Immunol. Methods 188 (1995) 9-19.
Billah, M. M., ET AL., Bioelectrochem. 80 (2010) 49-54.
Persson, H., ET AL., Infect. Immun. 81 (2013) 2236-2241.

The following examples and figures are provided to aid the understanding of the present invention, the true scope of which is set forth in the appended claims. It is understood that modifications can be made in the procedures set forth without departing from the spirit of the invention.

EXAMPLES

Figure 1:
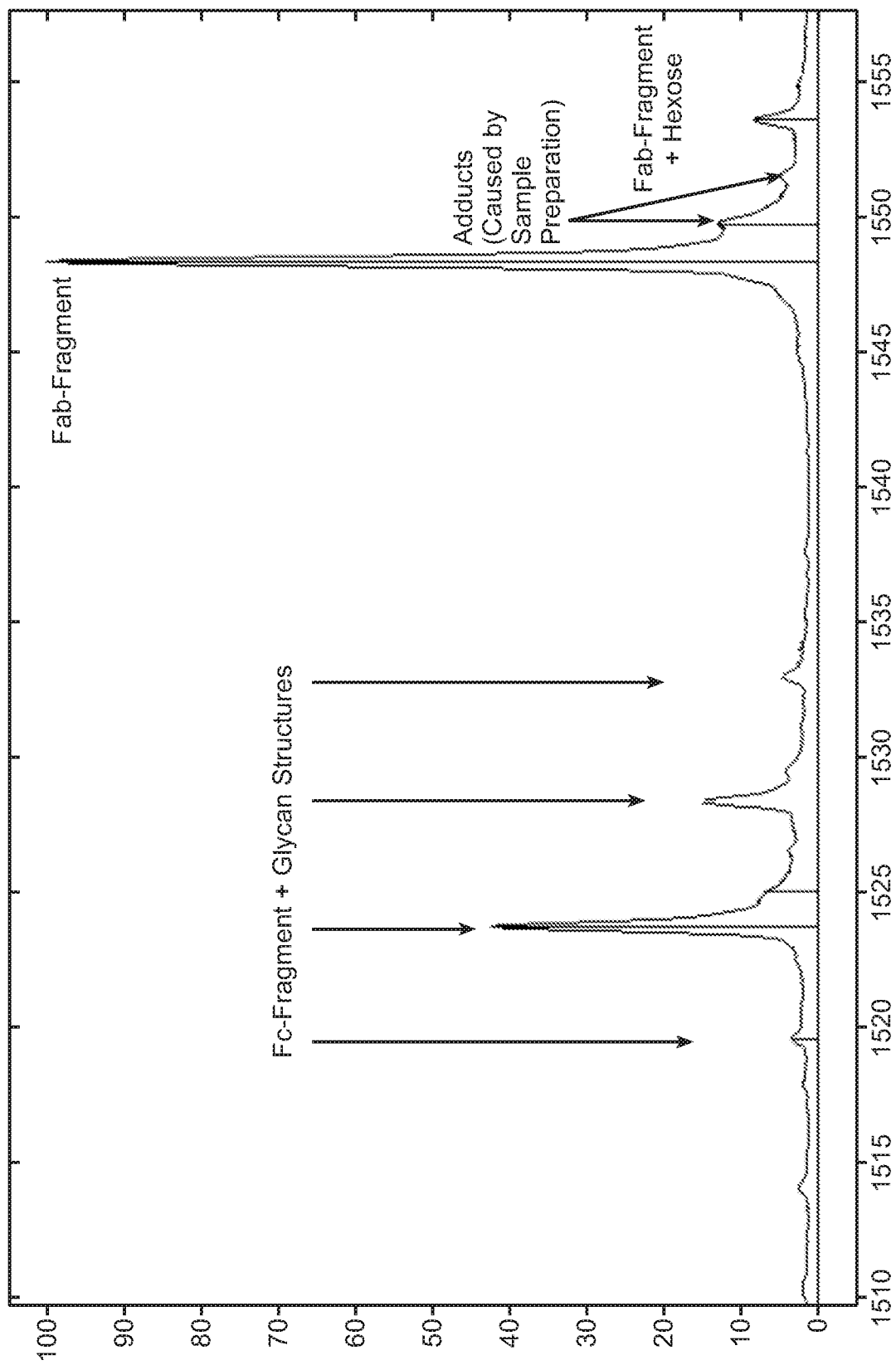
FIG. 1 UHR ESI-QTOF mass spectrometry of bevacizumab digested with lysine-gingipain of *Porphyromonas gingivalis* for one hour at 37° C. Only Fab and Fc fragments were detected.
Figure 2:
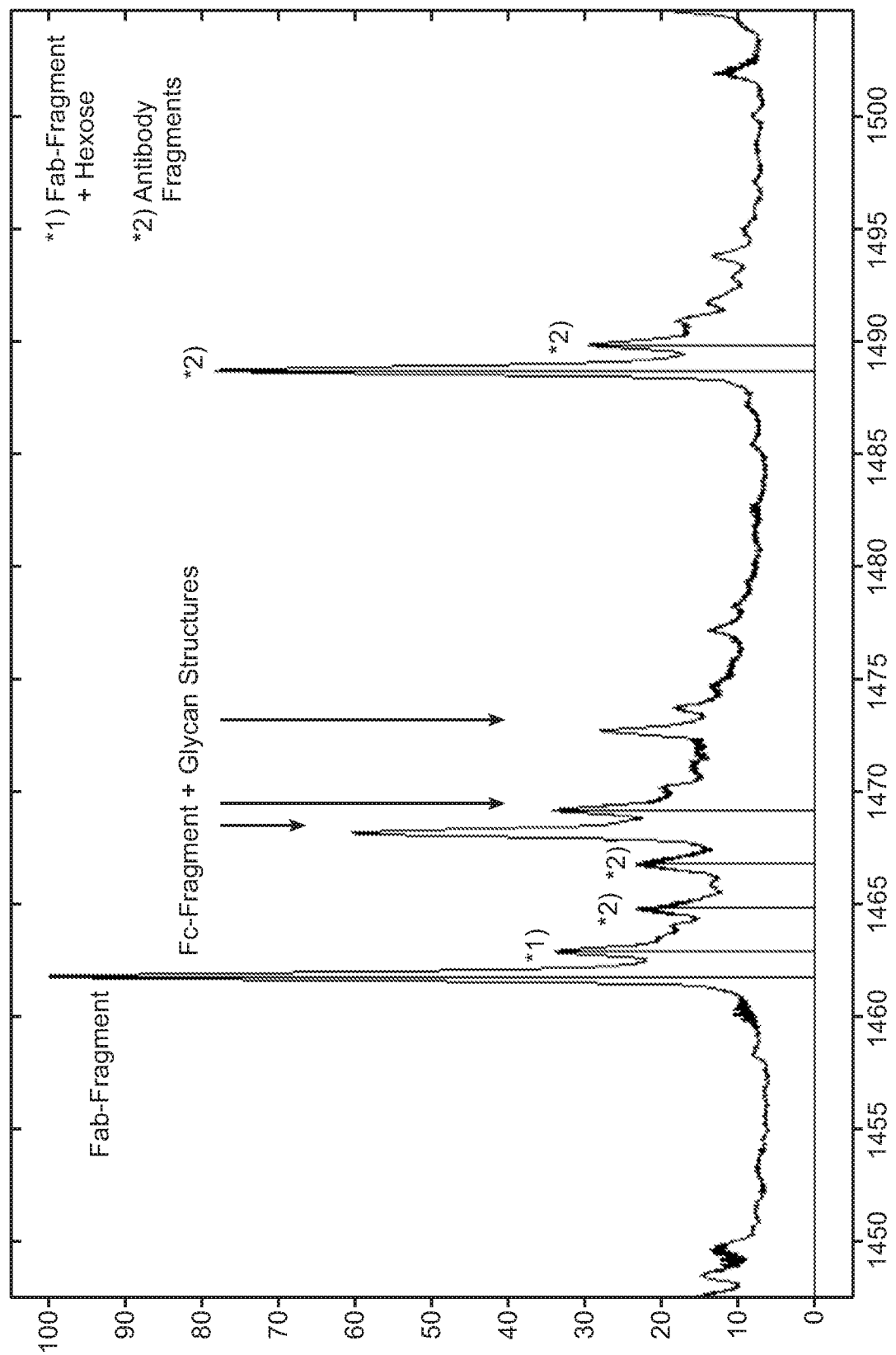
FIG. 2 UHR ESI-QTOF mass spectrometry of bevacizumab digested with papain for 1.5 h at 37° C. Beside Fab and Fc fragments, several Fab- and antibody fragments were detected.
Figure 3:
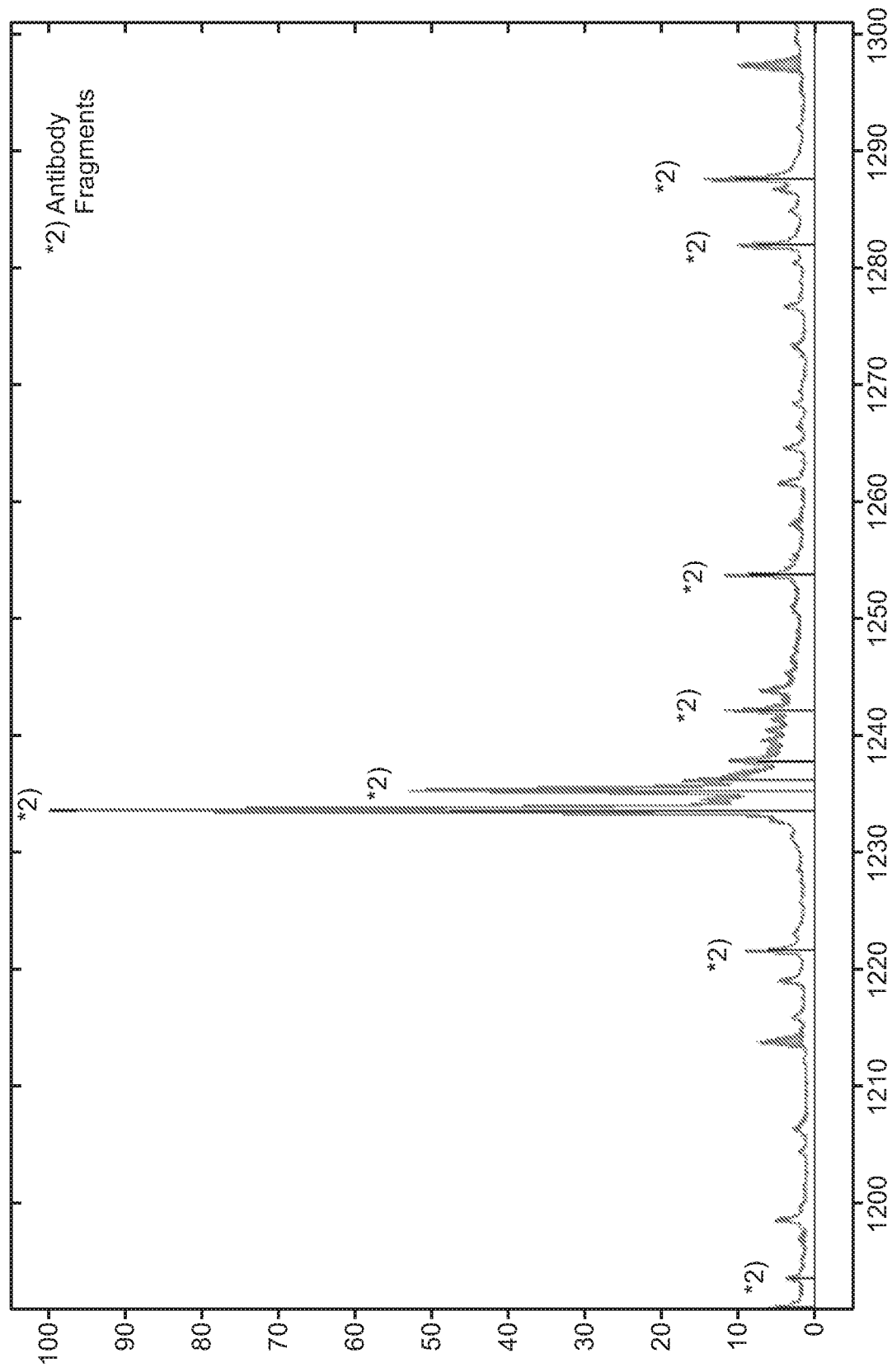
FIG. 3 UHR ESI-QTOF mass spectrometry of bevacizumab digested with papain for 2 h at 37° C. Several antibody fragments were detected. Fab and Fc fragment could not be identified.
Figure 4A:
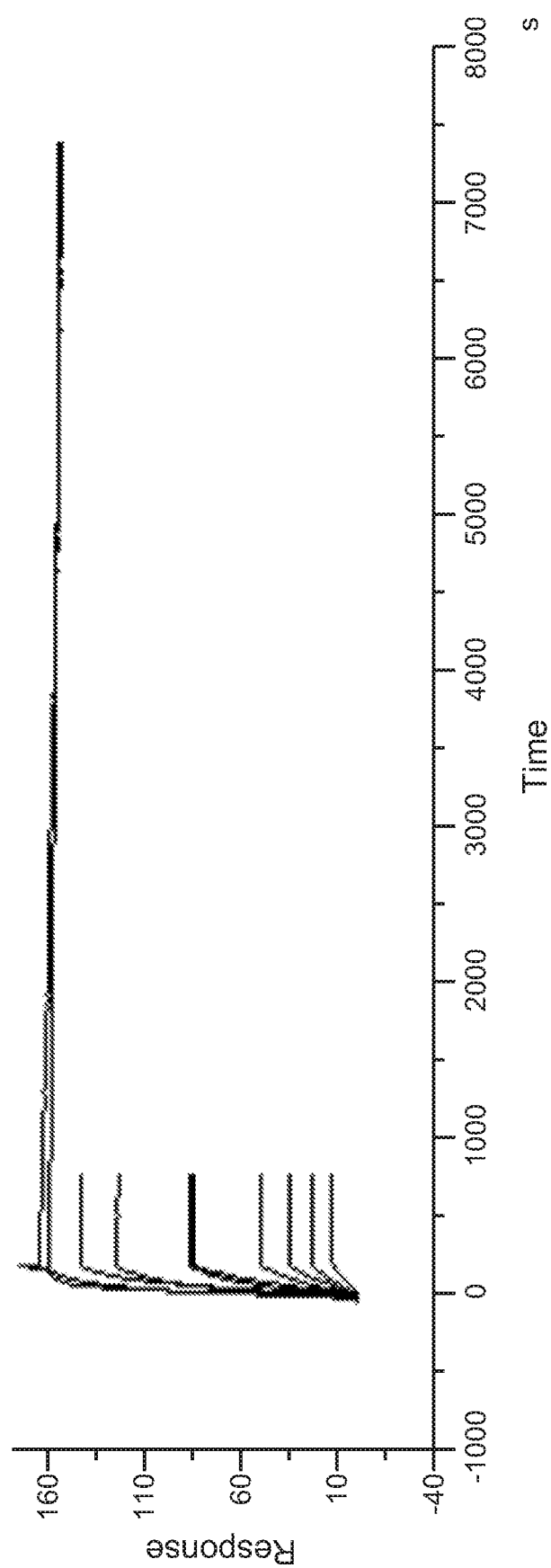
FIG. 4A Surface plasmon resonance sensorgrams of bevacizumab.
Figure 4B:
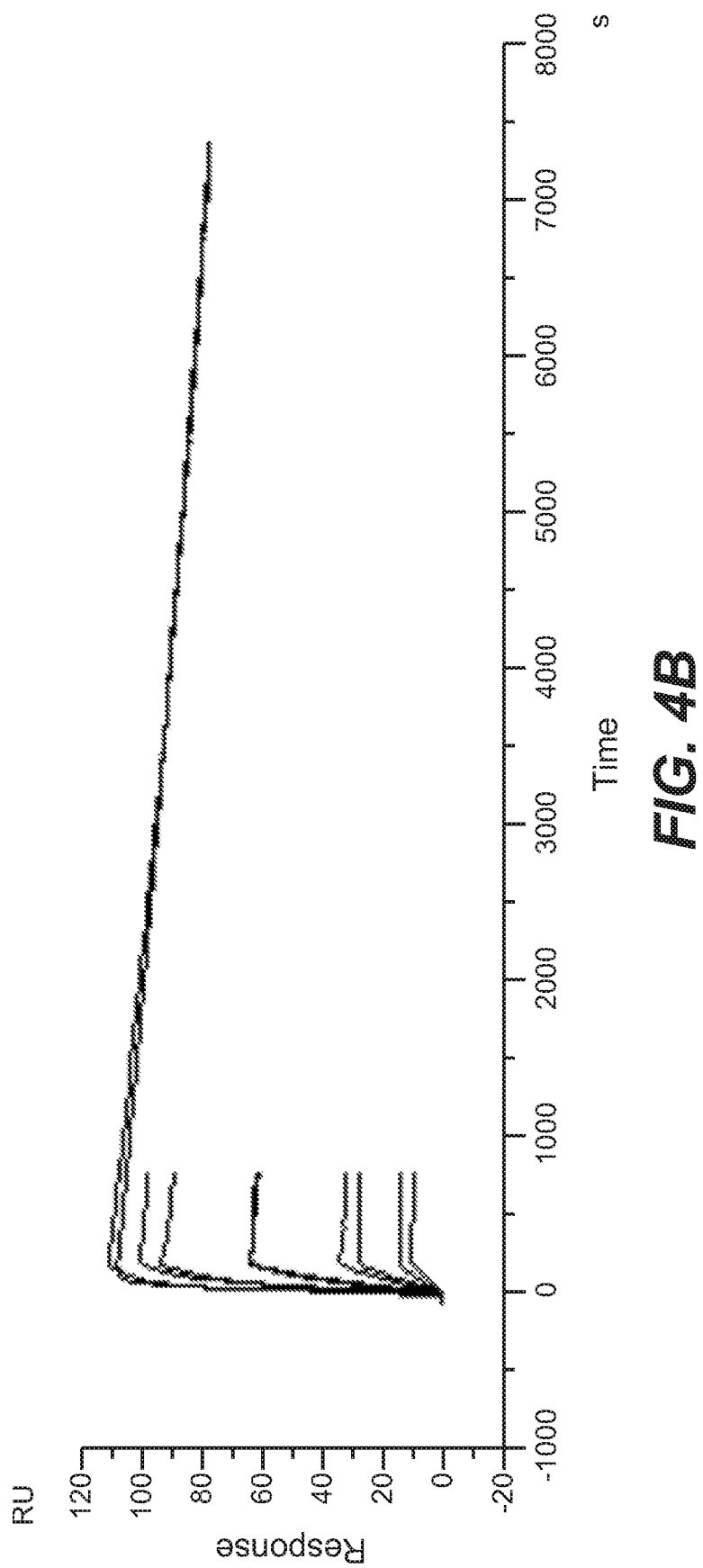
FIG. 4B Surface plasmon resonance sensorgrams of a recombinant bevacizumab Fab.
Figure 4C:
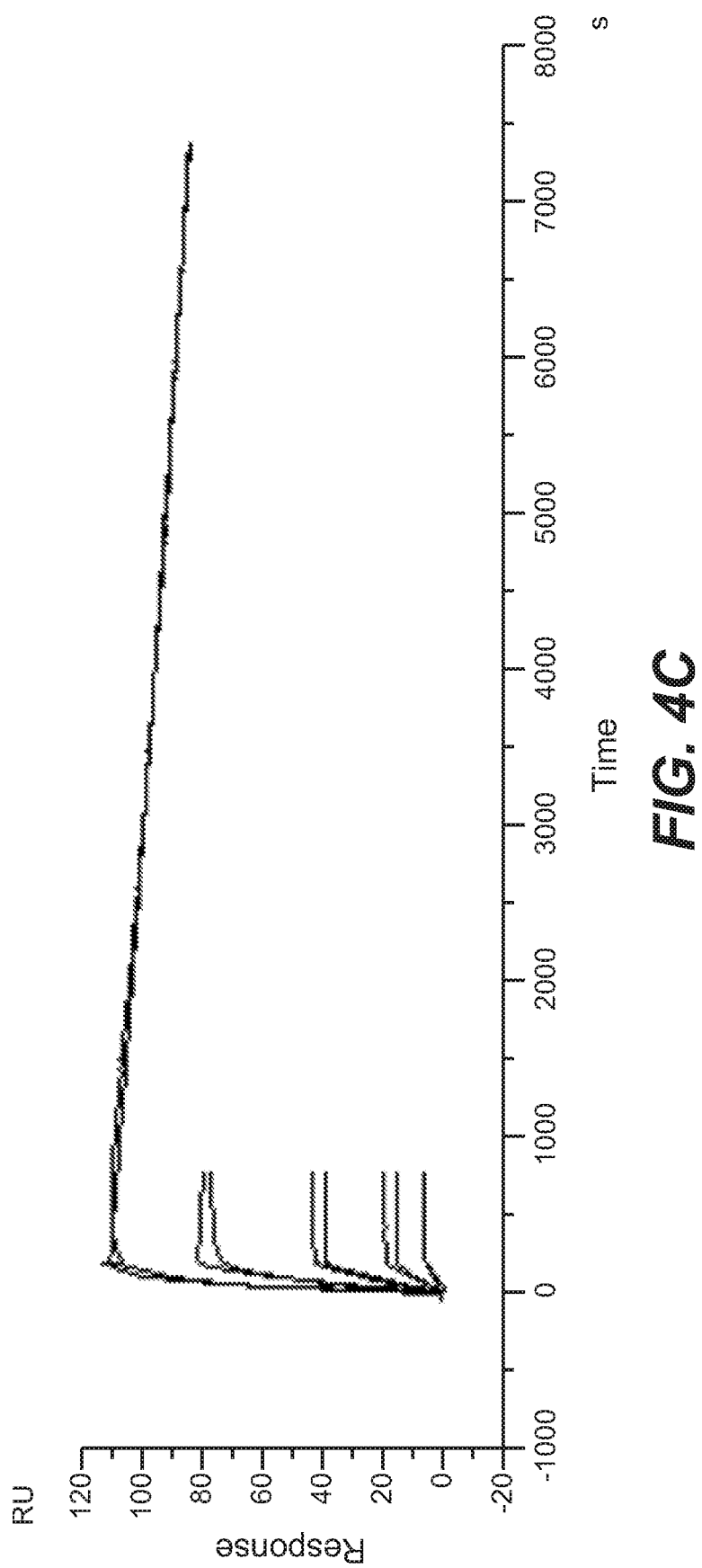
FIG. 4C Surface plasmon resonance sensorgrams of bevacizumab digested with lysine-gingipain of *Porphyromonas gingivalis*.
Figure 4D:
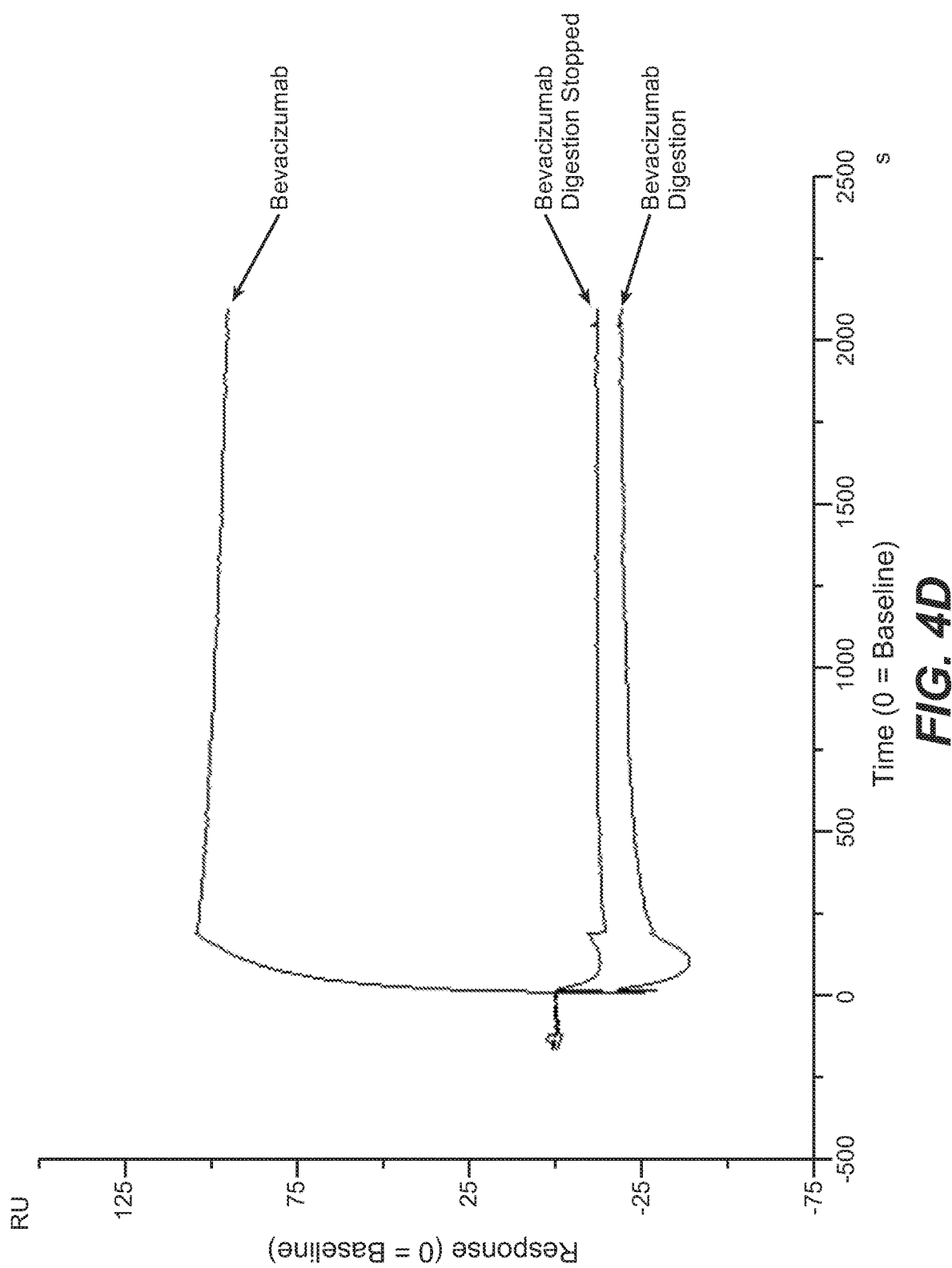
FIG. 4D Surface plasmon resonance sensorgrams of bevacizumab, bevacizumab digested with papain without termination of the digest, and bevacizumab digested with papain with termination of the digest.

Bevacizumab was obtained from Roche Diagnostics GmbH (Mannheim, Germany). Papain was obtained as suspension with a concentration of 10 mg/mL from Sigma-Aldrich/Roche Diagnostics GmbH. Lysine-gingipain of *Porphyromonas gingivalis* was obtained under the trade name GingisKHAN® from Genovis (Lund, Sweden). GingisKHAN® was reconstituted in 200 µL double distilled water (ddH2O) resulting in 2000 U/200 µL, and the 10× reducing agent was freshly prepared in 50 µL ddH2O (final concentration: 20 mM cysteine) prior to each digestion.

Example 1

Transient Fab Expression and Purification

The antibody light chain and heavy chain Fd-fragments were ordered as gene syntheses and cloned via unique restriction sites using standard cloning procedures into separate expression vectors for each chain enabling secretory expression in HEK cells growing in suspension. Transfection (1:1 plasmid ratios) into HEK293-F cells (Invitrogen, Cat. No. 510029) was performed according to the cell supplier's instructions using Maxiprep (Qiagen, Cat. No. 12163) preparations of the antibody vectors, Opti-MEM I medium (Invitrogen, Cat. No. 31985) 293fectin (Invitrogen, Cat. No. 31985070), and an initial cell density of 1-2×10E+06 viable cells/mL in serum-free FreeStyle 293 expression medium (Invitrogen, Cat. No. 12338018). Antibody containing cell culture supernatants were harvested after 7 days of cultivation in shake flasks by centrifugation at 14,000×g for 30 min. and filtered through a 0.22 µm sterile filter (Thermo Scientific, Cat. No. 566-0020). The antibodies were purified directly from the supernatant, or the supernatant was stored at −80° C. until purification. The quality of the purified Fab was analyzed by SEC and BioAnalyzer.

Example 2

Enzymatic Cleavage of Bevacizumab with Papain
Without Purification:
The antibody was diluted in 20 mM Histidine, 140 mM NaCl, pH 6.0 to a final concentration of 1 mg/mL, added 2 µL 250 mM L-cysteine (Sigma-Aldrich, Schnelldorf, Germany) and 10.9 µL diluted papain (7.34 U/mL in 20 mM Histidine, 140 mM NaCl, pH 6.0), and incubated 1 h at 37° C.
With Purification:
The antibody was incubated with Papain (0.8 U/mg mAb; Sigma-Aldrich/Roche) in presence of 5 mM Cystein for 170 minutes at 37° C. To isolate the Fab from non-cleaved antibodies, Fc-fragments and Papain, the mixture was applied to a CaptureSelect IgG-CH1 and MabSelectSuRe affinity chromatography (GE Healthcare) according to manufacturer protocol. Finally, a size exclusion chromatography using a Superdex 75 10/300 GL column (GE Healthcare) was performed using 140 mM NaCl, 20 mM histidine (pH 6.0) as running buffer. Protein concentration of the Fab was determined by measuring the optical density (OD) at 280 nm, using the molar extinction coefficient calculated on the basis of the amino acid sequence. The purity was analyzed by SDS-PAGE in the presence and absence of a reducing agent (5 mM 1,4-dithiotreitol) and staining with Coomassie brilliant blue.

Example 3

Enzymatic Cleavage of Bevacizumab with Lysine-Gingipain of *Porphyromonas Gingivalis*

GingisKHAN was reconstituted in 200 µL ddH2O resulting in 2000 U/200 µL, and the 10× reducing agent was freshly prepared in 50 µL ddH2O (final concentration: 20 mM Cysteine) prior to each digestion. 100 µg antibody was diluted to a final concentration of 1 mg/mL in 100 mM Tris, pH 8.0 and subsequently digested with 10 µL GingisKHAN and 11 µL of freshly prepared 10× reducing agent at 37° C. for 1 hour.

Example 4

ESI-QTOF Mass Spectrometry
Samples were desalted by HPLC on a Sephadex G25 column (Kronlab, 5×250 mm, TAC05/250G0-SR) using 40% acetonitrile with 2% formic acid (v/v). The total mass was determined via ESI-QTOF MS on a maXis 4G UHR-QTOF MS system (Bruker Daltonik) equipped with a TriVersa NanoMate source (Advion). Calibration was performed with sodium iodide (Waters ToF G2-Sample Kit 2 Part: 700008892-1). For the recombinant and purified Fabs, data acquisition was done at 900-2600 m/z (ISCID: 0.0 eV), for the hIgG1s or digested hIgG1s, data acquisition was done at 900-4000 m/z (ISCID: 0.0 eV). The raw mass spectra were evaluated and transformed into individual relative molar masses using an in-house developed Roche software tool. For visualization of the results, the same in-house developed software was used to generate deconvoluted mass spectra.

Example 5

Surface Plasmon Resonance

Binding affinities and kinetics were investigated by surface plasmon resonance using a BIACORE™ T200 instrument (GE Healthcare). All experiments were performed at 25° C. using PBS-T (10 mM $Na_2HPO_4$, 140 mM NaCl, 0.05% TWEEN® 20, pH 7.4) as running and dilution buffer. An anti-His-tag (GE Healthcare, #28995056) or an anti-human Fab antibody (GE Healthcare, #28958325) was immobilized on a Series S CM5 Sensor Chip (GE Healthcare, #29104988) using standard amine coupling chemistry. Histidine-tagged human VEGF or full length IgG/Fabs were captured on the surface leading to a response between 10 and 50 RU. The analytes were injected for 180 s at concentrations from 2.2 nM up to 1800 nM onto the surface (association phase) at a flow rate of 30 μL/min. The dissociation phase was monitored for up to 3600 seconds by washing with running buffer. The surface was regenerated by injecting 10 mM Glycine pH 1.5 for 60 seconds at a flow rate of 5 μL/min. Bulk refractive index differences were corrected by subtracting the response obtained from a mock surface and by subtracting blank injections (double referencing). The derived curves were fitted to a 1:1 Langmuir binding model using the BIAevaluation software.

What is claimed is:

1. A method for determining the binding affinity of the binding sites of a bivalent full length antibody of the human immunoglobulin G type 1 (IgG1) isotype to a homo-multimeric antigen comprising the following steps:
    incubating a mixture comprising the antibody and lysine-gingipain of *Porphyromonas gingivalis* at a pH of 7.5 to 8.5, in the presence of a reducing agent, at a temperature of 30° C. to 42° C., for a time of 10 minutes to 240 minutes to cleave the antibody into antigen-binding fragments (Fabs) and C-terminal fragment, crystallizing fragment-(Fc)-region, and
    determining the binding affinity of the Fabs of the antibody for its antigen using surface plasmon resonance by directly applying the incubated reaction mixture obtained in the previous step in the surface plasmon resonance method,
    thereby determining the binding affinity of the binding sites of the bivalent full length antibody of the human IgG1 isotype.

2. The method according to claim 1, wherein the lysine-gingipain of *Porphyromonas gingivalis* has the amino acid sequence of SEQ ID NO: 2, SEQ ID NO: 3, or SEQ ID NO: 4.

3. The method according to claim 1, wherein the lysine-gingipain of *Porphyromonas gingivalis* has an amino acid sequence that comprises at least residues 230 to 739 of SEQ ID NO: 1.

4. The method according to claim 1, wherein the reducing agent is selected from the group consisting of 2-mercaptoethanol, cysteine, and dithiothreitol.

5. The method according to claim 4, wherein the reducing agent is cysteine.

6. The method according to claim 1, wherein the reducing agent is cysteine at a concentration of 0.5 mM to 10 mM.

7. The method according to claim 1, wherein the pH value is about pH 8.

8. The method according to claim 1, wherein the incubating is at a temperature of 35° C. to 38° C.

9. The method according to claim 1, wherein the incubating is for a time of about 60 minutes.

10. The method according to claim 1, wherein the antibody comprises in the Fc-region the mutations P329G, L234A and L235A in both heavy chain polypeptides.

11. A method for selecting an antibody specifically binding to a homo-multimeric antigen comprising the following steps:
providing a plurality of bivalent full length antibodies of the human IgG1 isotype binding to the same homo-multimeric antigen,
determining the binding affinity of each of the antibodies of the plurality of antibodies to its antigen with a method according to claim 1, and
selecting one or more antibodies based on the binding affinity determined in the previous step.

12. The method according to claim 1, wherein the incubated mixture is used for the determination of the binding affinity without intermediate purification.

13. The method according to claim 2, wherein the antibody comprises in the Fc-region the mutations P329G, L234A and L235A in both heavy chain polypeptides.

14. The method according to claim 13, wherein the incubated mixture is used for the determination of the binding affinity without intermediate purification.

15. The method according to claim 14, wherein the reducing agent is selected from the group consisting of 2-mercaptoethanol, cysteine, and dithiothreitol.

16. The method according to claim 15, wherein the reducing agent is cysteine.

17. The method according to claim 15, wherein the reducing agent is cysteine at a concentration of 0.5 mM to 10 mM.

18. The method according to claim 15, wherein the pH value is about pH 8.

19. The method according to claim 18, wherein the incubating is at a temperature of 35° C. to 38° C.

20. The method according to claim 19, wherein the incubating is for a time of about 60 minutes.

21. The method of claim 1, wherein the homomultimeric antigen is vascular endothelial growth factor-A (VEGF-A), carcinoembryonic antigen (CEA), angiopoietin-2 (ANG2), or fibroblast activation protein (FAP).

22. The method of claim 11, wherein the homomultimeric antigen is vascular endothelial growth factor-A (VEGF-A), carcinoembryonic antigen (CEA), angiopoietin-2 (ANG2), or fibroblast activation protein (FAP).

* * * * *